United States Patent
Martinson et al.

(10) Patent No.: US 8,740,879 B2
(45) Date of Patent: *Jun. 3, 2014

(54) INSTRUMENTED ORTHOPEDIC AND OTHER MEDICAL IMPLANTS

(75) Inventors: James B. Martinson, Minnetonka, MN (US); John G. Stark, Deephaven, MN (US); Timothy J. B. Hanson, Plymouth, MN (US); Steven Backes, Minneapolis, MN (US)

(73) Assignee: IZEX Technologies, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,232

(22) Filed: Sep. 12, 2012

(65) Prior Publication Data

US 2013/0066426 A1    Mar. 14, 2013

Related U.S. Application Data

(63) Continuation of application No. 11/494,719, filed on Jul. 27, 2006, now Pat. No. 8,491,572, which is a continuation of application No. PCT/US2005/041339, filed on Nov. 15, 2005.

(60) Provisional application No. 60/722,361, filed on Sep. 30, 2005, provisional application No. 60/628,050, filed on Nov. 15, 2004.

(51) Int. Cl.
     *A61K 9/22*      (2006.01)

(52) U.S. Cl.
     USPC .................. 604/891.1; 604/890.1; 128/903

(58) Field of Classification Search
     USPC ........ 600/587, 325, 377, 300; 607/48, 51, 57, 607/60; 623/24; 128/903; 604/891.1, 890.1, 604/502, 93.01, 288.01
See application file for complete search history.

(56) References Cited

U.S. PATENT DOCUMENTS

| 2,693,796 A | 11/1954 | Warner |
| 2,777,439 A | 1/1957 | Tuttle |

(Continued)

FOREIGN PATENT DOCUMENTS

| EP | 173161 A1 | 3/1986 |
| GB | 2177603 A | 1/1987 |

(Continued)

OTHER PUBLICATIONS

"U.S. Appl. No. 09/329,880, Notice of Allowance mailed Mar. 15, 2001", 6 pgs.

(Continued)

*Primary Examiner* — Kevin C. Sirmons
*Assistant Examiner* — Deanna K Hall
(74) *Attorney, Agent, or Firm* — Schwegman, Lundberg & Woessner, P.A.

(57) ABSTRACT

Medical implants can comprise various instrumentation to impart desirable functionality to the implant. In some embodiments, the implants comprise functional structures, such as sensors, energy propagating transducers, drug delivery systems and the like. Additional instrumentation to facilitate the functionality of these devices can include, for example, microprocessors, communication systems, power sources or the like. Drug delivery systems can comprise, for example, an isolated reservoir with a control system to control the delivery of a biological agent from the reservoir. The implants can be orthopedic implants that are designed to interface with a patient's skeletal system wherein the orthopedic implant may itself embody sensors, processors, power supplies, memory and/or communication capability.

20 Claims, 6 Drawing Sheets

(56) References Cited

U.S. PATENT DOCUMENTS

| | | |
|---|---|---|
| 2,832,334 A | 4/1958 | Whitelaw |
| 3,253,588 A | 5/1966 | Vuilleumier et al. |
| 3,374,675 A | 3/1968 | Keropian |
| 3,495,824 A | 2/1970 | Cuinier |
| 3,521,623 A | 7/1970 | Nichols et al. |
| 3,667,457 A | 6/1972 | Zumaglini |
| 3,734,087 A | 5/1973 | Sayer et al. |
| 3,866,604 A | 2/1975 | Curless et al. |
| 3,929,335 A | 12/1975 | Malick et al. |
| 3,976,057 A | 8/1976 | Barclay |
| 3,986,498 A | 10/1976 | Lewis |
| 4,037,480 A | 7/1977 | Wagner |
| 4,135,503 A | 1/1979 | Romano |
| 4,178,923 A | 12/1979 | Curlee |
| 4,235,437 A | 11/1980 | Ruis et al. |
| 4,256,094 A | 3/1981 | Kapp et al. |
| 4,306,571 A | 12/1981 | Mcleod, Jr. |
| 4,323,080 A | 4/1982 | Melhart |
| 4,331,133 A | 5/1982 | Arkans |
| 4,354,676 A | 10/1982 | Ariel |
| 4,375,217 A | 3/1983 | Arkans |
| 4,396,010 A | 8/1983 | Arkans |
| 4,397,308 A | 8/1983 | Hepburn |
| 4,407,496 A | 10/1983 | Johnson |
| 4,408,559 A | 10/1983 | Sugiura |
| 4,408,599 A | 10/1983 | Mummert |
| 4,419,988 A | 12/1983 | Mummert |
| 4,422,634 A | 12/1983 | Hopkins |
| 4,426,884 A | 1/1984 | Polchaninoff |
| 4,436,099 A | 3/1984 | Raftopoulos |
| 4,436,303 A | 3/1984 | McKillip et al. |
| 4,485,808 A | 12/1984 | Hepburn |
| 4,501,148 A | 2/1985 | Nicholas et al. |
| 4,508,111 A | 4/1985 | Hepburn |
| 4,512,567 A | 4/1985 | Phillips |
| 4,520,804 A | 6/1985 | DiGeorge |
| 4,522,213 A | 6/1985 | Wallroth |
| 4,538,595 A | 9/1985 | Hajianpour |
| 4,538,600 A | 9/1985 | Hepburn |
| 4,544,154 A | 10/1985 | Ariel |
| 4,548,208 A | 10/1985 | Niemi |
| 4,553,124 A | 11/1985 | Malicki |
| 4,556,216 A | 12/1985 | Pitkanen |
| 4,576,158 A | 3/1986 | Boland |
| 4,586,495 A | 5/1986 | Petrofsky |
| 4,590,925 A | 5/1986 | Dillon |
| 4,604,098 A | 8/1986 | Seamone et al. |
| 4,620,532 A | 11/1986 | Housewerth |
| 4,621,620 A | 11/1986 | Anderson |
| 4,624,246 A | 11/1986 | Ajemian |
| 4,645,199 A | 2/1987 | Bloemendaal |
| 4,651,719 A | 3/1987 | Funk et al. |
| 4,653,479 A | 3/1987 | Maurer |
| 4,654,010 A | 3/1987 | Havriluk |
| 4,681,097 A | 7/1987 | Pansiera |
| 4,697,808 A | 10/1987 | Larson et al. |
| 4,711,242 A | 12/1987 | Petrofsky |
| 4,716,889 A | 1/1988 | Saringer |
| 4,718,665 A | 1/1988 | Airy et al. |
| 4,757,453 A | 7/1988 | Nasiff |
| 4,762,134 A | 8/1988 | Gala |
| 4,763,901 A | 8/1988 | Richter |
| 4,785,674 A | 11/1988 | Orman et al. |
| 4,796,641 A | 1/1989 | Mills et al. |
| 4,801,138 A | 1/1989 | Airy et al. |
| 4,815,469 A | 3/1989 | Cohen et al. |
| 4,817,588 A | 4/1989 | Bledsoe |
| 4,822,336 A | 4/1989 | Ditraglia |
| 4,825,852 A | 5/1989 | Genovese et al. |
| 4,828,257 A | 5/1989 | Dyer et al. |
| 4,830,021 A | 5/1989 | Thornton |
| 4,836,218 A | 6/1989 | Gay et al. |
| 4,839,822 A | 6/1989 | Dormond et al. |
| 4,848,152 A | 7/1989 | Pratt, Jr. |
| 4,858,620 A | 8/1989 | Sugarman et al. |
| 4,863,157 A | 9/1989 | Mendel et al. |
| 4,875,469 A | 10/1989 | Brook et al. |
| 4,905,560 A | 3/1990 | Suzuki et al. |
| 4,909,262 A | 3/1990 | Halpern et al. |
| 4,912,638 A | 3/1990 | Pratt, Jr. |
| 4,913,163 A | 4/1990 | Roger et al. |
| 4,922,925 A | 5/1990 | Crandall et al. |
| 4,928,674 A | 5/1990 | Halperin et al. |
| 4,928,959 A | 5/1990 | Bassett et al. |
| 4,930,497 A | 6/1990 | Saringer |
| 4,934,694 A | 6/1990 | McIntosh |
| 4,944,288 A | 7/1990 | Rawcliffe |
| 4,952,928 A | 8/1990 | Carroll et al. |
| 4,958,632 A | 9/1990 | Duggan |
| 4,958,645 A | 9/1990 | Cadell et al. |
| 4,971,069 A | 11/1990 | Gracovetsky |
| 4,988,981 A | 1/1991 | Zimmerman et al. |
| 5,000,169 A | 3/1991 | Swicegood et al. |
| 5,003,965 A | 4/1991 | Talish et al. |
| 5,012,820 A | 5/1991 | Meyer |
| 5,013,037 A | 5/1991 | Stermer |
| 5,019,974 A | 5/1991 | Beckers |
| 5,020,795 A | 6/1991 | Airy et al. |
| 5,031,604 A | 7/1991 | Dye |
| 5,042,504 A | 8/1991 | Huberti |
| 5,050,618 A | 9/1991 | Larsen |
| 5,052,375 A | 10/1991 | Stark et al. |
| 5,052,379 A | 10/1991 | Airy et al. |
| 5,054,771 A | 10/1991 | Mansfield |
| 5,078,152 A | 1/1992 | Bond et al. |
| 5,090,421 A | 2/1992 | Wagoner, III |
| 5,116,296 A | 5/1992 | Watkins et al. |
| 5,121,747 A | 6/1992 | Andrews |
| 5,125,412 A | 6/1992 | Thornton |
| 5,133,732 A | 7/1992 | Wiktor |
| 5,135,536 A | 8/1992 | Hillstead |
| 5,153,584 A | 10/1992 | Engira |
| 5,178,160 A | 1/1993 | Gracovetsky et al. |
| 5,181,902 A | 1/1993 | Erickson et al. |
| 5,186,163 A | 2/1993 | Dye |
| 5,195,941 A | 3/1993 | Erickson et al. |
| 5,209,712 A | 5/1993 | Ferri |
| 5,211,161 A | 5/1993 | Stef |
| 5,218,954 A | 6/1993 | Van Bemmelen |
| 5,239,987 A | 8/1993 | Kaiser et al. |
| 5,252,102 A | 10/1993 | Singer |
| 5,255,188 A | 10/1993 | Telepko |
| 5,263,491 A | 11/1993 | Thornton |
| 5,265,010 A | 11/1993 | Evans-Paganelli et al. |
| 5,280,265 A | 1/1994 | Kramer et al. |
| 5,280,783 A | 1/1994 | Focht et al. |
| 5,282,460 A | 2/1994 | Boldt |
| 5,284,131 A | 2/1994 | Gray |
| 5,287,546 A | 2/1994 | Tesic et al. |
| 5,297,540 A | 3/1994 | Kaiser et al. |
| 5,307,791 A | 5/1994 | Senoue et al. |
| 5,335,674 A | 8/1994 | Siegler |
| 5,336,245 A | 8/1994 | Adams et al. |
| 5,337,758 A | 8/1994 | Moore et al. |
| 5,338,157 A | 8/1994 | Blomquist |
| 5,354,162 A | 10/1994 | Burdea et al. |
| 5,360,392 A | 11/1994 | Mccoy |
| 5,368,546 A | 11/1994 | Stark et al. |
| 5,373,852 A | 12/1994 | Harrison et al. |
| 5,391,141 A | 2/1995 | Hamilton |
| 5,396,896 A | 3/1995 | Tumey et al. |
| 5,410,472 A | 4/1995 | Anderson |
| 5,417,643 A | 5/1995 | Taylor |
| 5,425,750 A | 6/1995 | Moberg |
| 5,435,321 A | 7/1995 | Mcmillen et al. |
| 5,437,610 A | 8/1995 | Cariapa et al. |
| 5,437,617 A | 8/1995 | Heinz et al. |
| 5,443,440 A | 8/1995 | Tumey et al. |
| 5,452,205 A | 9/1995 | Telepko |
| 5,453,075 A | 9/1995 | Bonutti et al. |
| 5,462,504 A | 10/1995 | Trulaske et al. |
| 5,466,213 A | 11/1995 | Hogan et al. |
| 5,474,083 A | 12/1995 | Church et al. |
| 5,474,088 A | 12/1995 | Zaharkin et al. |

(56) References Cited

U.S. PATENT DOCUMENTS

| | | |
|---|---|---|
| 5,474,090 A | 12/1995 | Begun et al. |
| 5,476,441 A | 12/1995 | Durfee et al. |
| 5,484,389 A | 1/1996 | Stark et al. |
| 5,515,858 A | 5/1996 | Myllymaeki |
| 5,520,622 A | 5/1996 | Bastyr et al. |
| 5,538,005 A | 7/1996 | Harrison et al. |
| 5,553,609 A | 9/1996 | Chen et al. |
| 5,556,421 A | 9/1996 | Prutchi et al. |
| 5,558,627 A | 9/1996 | Singer et al. |
| 5,569,120 A | 10/1996 | Anjanappa et al. |
| 5,579,378 A | 11/1996 | Arlinghaus, Jr. |
| 5,583,758 A | 12/1996 | McIlroy et al. |
| 5,586,067 A | 12/1996 | Gross et al. |
| 5,597,373 A | 1/1997 | Bond et al. |
| 5,625,882 A | 4/1997 | Vook |
| 5,662,693 A | 9/1997 | Johnson et al. |
| 5,671,733 A | 9/1997 | Raviv et al. |
| 5,683,351 A | 11/1997 | Kaiser et al. |
| 5,704,364 A | 1/1998 | Saltzstein et al. |
| 5,713,841 A | 2/1998 | Graham |
| 5,722,418 A | 3/1998 | Bro |
| 5,751,959 A | 5/1998 | Sato et al. |
| 5,754,121 A | 5/1998 | Ward et al. |
| 5,772,611 A | 6/1998 | Hocherman |
| 5,775,332 A | 7/1998 | Goldman |
| 5,778,618 A | 7/1998 | Abrams |
| 5,785,666 A | 7/1998 | Costello et al. |
| 5,792,077 A | 8/1998 | Gomes |
| 5,792,085 A | 8/1998 | Walters |
| 5,801,756 A | 9/1998 | Iizawa |
| 5,823,975 A | 10/1998 | Stark et al. |
| 5,827,209 A | 10/1998 | Gross |
| 5,830,162 A | 11/1998 | Giovannetti |
| 5,836,304 A | 11/1998 | Kellinger et al. |
| 5,842,175 A | 11/1998 | Andros et al. |
| 5,843,120 A | 12/1998 | Israel et al. |
| 5,851,193 A | 12/1998 | Arikka et al. |
| 5,868,647 A | 2/1999 | Belsole |
| 5,882,203 A | 3/1999 | Correa et al. |
| 5,888,173 A | 3/1999 | Singhal |
| 5,890,997 A | 4/1999 | Roth |
| 5,908,383 A | 6/1999 | Brynjestad |
| 5,913,310 A | 6/1999 | Brown |
| 5,915,240 A | 6/1999 | Karpf |
| 5,918,603 A | 7/1999 | Brown |
| 5,929,782 A | 7/1999 | Stark et al. |
| 5,935,086 A | 8/1999 | Beacon et al. |
| 5,935,162 A | 8/1999 | Dang |
| 5,940,801 A | 8/1999 | Brown |
| 5,954,621 A | 9/1999 | Joutras et al. |
| 5,961,446 A | 10/1999 | Beller et al. |
| 5,980,435 A | 11/1999 | Joutras et al. |
| 5,980,447 A | 11/1999 | Trudeau |
| 5,989,157 A | 11/1999 | Walton |
| 5,997,476 A | 12/1999 | Brown |
| 6,007,459 A | 12/1999 | Burgess |
| 6,012,926 A | 1/2000 | Hodges et al. |
| 6,014,432 A | 1/2000 | Modney |
| 6,014,631 A | 1/2000 | Teagarden et al. |
| 6,029,138 A | 2/2000 | Khorasani et al. |
| 6,039,688 A | 3/2000 | Douglas et al. |
| 6,050,924 A | 4/2000 | Shea |
| 6,053,873 A | 4/2000 | Govari et al. |
| 6,059,506 A | 5/2000 | Kramer |
| 6,059,692 A | 5/2000 | Hickman |
| 6,119,516 A | 9/2000 | Hock |
| 6,123,861 A | 9/2000 | Santini et al. |
| 6,127,596 A | 10/2000 | Brown et al. |
| 6,129,663 A | 10/2000 | Ungless et al. |
| 6,132,337 A | 10/2000 | Krupka et al. |
| 6,140,697 A | 10/2000 | Usami et al. |
| 6,161,095 A | 12/2000 | Brown |
| 6,162,189 A | 12/2000 | Girone et al. |
| 6,162,253 A | 12/2000 | Conzemius et al. |
| 6,166,518 A | 12/2000 | Echarri et al. |
| 6,168,563 B1 | 1/2001 | Brown |
| 6,171,237 B1 | 1/2001 | Avitall et al. |
| 6,177,940 B1 | 1/2001 | Bond et al. |
| 6,183,259 B1 | 2/2001 | Marci et al. |
| 6,184,797 B1 | 2/2001 | Stark et al. |
| 6,190,287 B1 | 2/2001 | Nashner |
| 6,198,971 B1 | 3/2001 | Leysieffer |
| 6,206,829 B1 | 3/2001 | Iliff |
| 6,224,486 B1 | 5/2001 | Walker |
| 6,231,344 B1 | 5/2001 | Merzenich et al. |
| 6,246,975 B1 | 6/2001 | Rivonelli et al. |
| 6,248,065 B1 | 6/2001 | Brown |
| 6,249,809 B1 | 6/2001 | Bro et al. |
| 6,270,457 B1 | 8/2001 | Bardy |
| 6,272,481 B1 | 8/2001 | Lawrence et al. |
| 6,283,761 B1 | 9/2001 | Joao |
| 6,283,923 B1 | 9/2001 | Finkelstein et al. |
| 6,296,595 B1 | 10/2001 | Stark et al. |
| 6,302,844 B1 | 10/2001 | Walker et al. |
| 6,312,378 B1 | 11/2001 | Bardy |
| 6,322,502 B1 | 11/2001 | Schoenberg et al. |
| 6,371,123 B1 | 4/2002 | Stark et al. |
| 6,413,190 B1 | 7/2002 | Wood |
| 6,413,279 B1 | 7/2002 | Metzger et al. |
| 6,442,413 B1 | 8/2002 | Silver |
| 6,471,723 B1 | 10/2002 | Ashworth et al. |
| 6,475,477 B1 | 11/2002 | Kohn et al. |
| 6,491,666 B1 | 12/2002 | Santini, Jr. et al. |
| 6,515,593 B1 | 2/2003 | Stark et al. |
| 6,530,954 B1 | 3/2003 | Eckmiller |
| 6,531,417 B2 | 3/2003 | Choi et al. |
| 6,540,707 B1 | 4/2003 | Stark et al. |
| 6,563,464 B2 | 5/2003 | Ballantine et al. |
| 6,572,543 B1 | 6/2003 | Christopherson et al. |
| 6,610,069 B2 | 8/2003 | Euteneuer et al. |
| 6,638,231 B2 | 10/2003 | Govari et al. |
| 6,641,540 B2 | 11/2003 | Fleischman et al. |
| 6,676,706 B1 | 1/2004 | Mears et al. |
| 6,689,056 B1 | 2/2004 | Kilcoyne et al. |
| 6,695,866 B1 | 2/2004 | Kuehn et al. |
| 6,706,005 B2 | 3/2004 | Roy et al. |
| 6,718,163 B2 | 4/2004 | Tandy |
| 6,781,284 B1 | 8/2004 | Pelrine et al. |
| 6,783,260 B2 | 8/2004 | Machi et al. |
| 6,783,499 B2 | 8/2004 | Schwartz |
| 6,790,227 B2 | 9/2004 | Burgermeister |
| 6,821,299 B2 | 11/2004 | Kirking et al. |
| 6,827,670 B1 | 12/2004 | Stark et al. |
| 6,850,804 B2 | 2/2005 | Eggers et al. |
| 6,858,220 B2 | 2/2005 | Greenberg et al. |
| 6,872,187 B1 | 3/2005 | Stark et al. |
| 6,875,208 B2 | 4/2005 | Santini, Jr. et al. |
| 6,937,736 B2 | 8/2005 | Toda |
| 6,939,377 B2 | 9/2005 | Jayaraman et al. |
| 7,104,955 B2 | 9/2006 | Bardy |
| 7,117,028 B2 | 10/2006 | Bardy |
| 7,226,442 B2 | 6/2007 | Sheppard, Jr. et al. |
| 7,251,609 B1 | 7/2007 | McAlindon et al. |
| 7,416,537 B1 | 8/2008 | Stark et al. |
| 8,308,794 B2 | 11/2012 | Martinson et al. |
| 8,491,572 B2 * | 7/2013 | Martinson et al. ......... 604/891.1 |
| 2002/0017834 A1 | 2/2002 | MacDonald |
| 2002/0029784 A1 | 3/2002 | Stark et al. |
| 2002/0177782 A1 | 11/2002 | Penner |
| 2002/0188282 A1 | 12/2002 | Greenberg |
| 2003/0032892 A1 | 2/2003 | Erlach et al. |
| 2003/0125017 A1 | 7/2003 | Greene et al. |
| 2003/0153819 A1 | 8/2003 | Lliff |
| 2003/0225331 A1 | 12/2003 | Diederich et al. |
| 2004/0034332 A1 | 2/2004 | Uhland |
| 2004/0073175 A1 | 4/2004 | Jacobson et al. |
| 2004/0102854 A1 | 5/2004 | Zhu |
| 2004/0106963 A1 | 6/2004 | Tsukamoto et al. |
| 2004/0143221 A1 | 7/2004 | Shadduck |
| 2004/0172083 A1 | 9/2004 | Penner |
| 2004/0176672 A1 | 9/2004 | Silver et al. |
| 2004/0220552 A1 | 11/2004 | Heruth et al. |
| 2004/0249675 A1 | 12/2004 | Stark et al. |
| 2005/0054988 A1 | 3/2005 | Rosenberg et al. |

(56) References Cited

U.S. PATENT DOCUMENTS

| | | |
|---|---|---|
| 2005/0113652 A1 | 5/2005 | Stark et al. |
| 2005/0113904 A1 | 5/2005 | Shank et al. |
| 2005/0187797 A1 | 8/2005 | Johnson |
| 2005/0273170 A1 | 12/2005 | Navarro et al. |
| 2006/0129050 A1 | 6/2006 | Martinson et al. |
| 2006/0244532 A1 | 11/2006 | Trifonov et al. |
| 2006/0271112 A1 | 11/2006 | Martinson et al. |
| 2007/0155588 A1 | 7/2007 | Stark et al. |
| 2008/0040153 A1 | 2/2008 | Davis, Jr. |
| 2008/0097143 A1 | 4/2008 | Califorrni |
| 2010/0121160 A1 | 5/2010 | Stark |
| 2012/0116806 A1 | 5/2012 | Stark et al. |
| 2012/0271200 A1 | 10/2012 | Martinson et al. |

FOREIGN PATENT DOCUMENTS

| | | |
|---|---|---|
| JP | 4-44708 A | 2/1992 |
| JP | 5-38684 A | 2/1993 |
| JP | 5-146476 A | 6/1993 |
| JP | 7-504102 A | 5/1995 |
| JP | 3023228 U | 4/1996 |
| JP | 9-84771 A | 3/1997 |
| JP | 9-114671 A | 5/1997 |
| NL | 7806327 | 12/1979 |
| NO | WO-95/22307 A1 | 8/1995 |
| SU | 1380747 A1 | 3/1988 |
| SU | 1750681 A1 | 7/1992 |
| WO | WO-95/01769 A2 | 1/1995 |
| WO | WO-96/04848 A1 | 2/1996 |
| WO | WO-96/20464 A1 | 7/1996 |
| WO | WO-96/36278 A1 | 11/1996 |
| WO | WO-98/37926 A1 | 9/1998 |
| WO | WO-98/42257 A1 | 10/1998 |
| WO | WO-00/12041 A2 | 3/2000 |
| WO | WO-00/40171 A2 | 7/2000 |
| WO | 01/26548 | 4/2001 |
| WO | WO-01/26548 A1 | 4/2001 |
| WO | WO-01/35473 A1 | 5/2001 |
| WO | WO-2004/093725 A2 | 11/2004 |
| WO | WO-2005/046514 A2 | 5/2005 |
| WO | WO-2005/082452 A1 | 9/2005 |
| WO | WO-2005/084257 A2 | 9/2005 |

OTHER PUBLICATIONS

"U.S. Appl. No. 09/329,880, Notice of Allowance mailed Jun. 8, 2000", 3 pgs.

"U.S. Appl. No. 09/329,880, Notice of Allowance mailed Oct. 29, 2001", 5 pgs.

"U.S. Appl. No. 09/339,071, Final Office Action mailed Jul. 13, 2007", 9 pgs.

"U.S. Appl. No. 09/339,071, Advisory Action mailed May 4, 2004", 3 pgs.

"U.S. Appl. No. 09/339,071, Advisory Action mailed Jun. 7, 2006", 5 pgs.

"U.S. Appl. No. 09/339,071, Advisory Action mailed Jul. 7, 2005", 3 pgs.

"U.S. Appl. No. 09/339,071, Examiner Interview Summary mailed Apr. 7, 2004", 4 pgs.

"U.S. Appl. No. 09/339,071, Examiner Interview Summary mailed Aug. 15, 2006", 3 pgs.

"U.S. Appl. No. 09/339,071, Final Office Action mailed Jan. 25, 2006", 13 pgs.

"U.S. Appl. No. 09/339,071, Final Office Action mailed Jan. 28, 2004", 13 pgs.

"U.S. Appl. No. 09/339,071, Final Office Action mailed Aug. 27, 2002", 10 pgs.

"U.S. Appl. No. 09/339,071, Final Office Action mailed Dec. 15, 2004", 13 pgs.

"U.S. Appl. No. 09/339,071, Non Final Office Action mailed May 21, 2003", 11 pgs.

"U.S. Appl. No. 09/339,071, Non Final Office Action mailed Jun. 24, 2004", 8 pgs.

"U.S. Appl. No. 09/339,071, Non Final Office Action mailed Aug. 2, 2005", 13 pgs.

"U.S. Appl. No. 09/339,071, Non Final Office Action mailed Oct. 12, 2006", 8 pgs.

"U.S. Appl. No. 09/339,071, Non Final Office Action mailed Nov. 15, 2007", 10 pgs.

"U.S. Appl. No. 09/339,071, Non Final Office Action mailed Dec. 17, 2001", 8 pgs.

"U.S. Appl. No. 09/339,071, Notice of Allowance mailed Apr. 23, 2008", 6 pgs.

"U.S. Appl. No. 09/339,071, Preliminary Amendment filed Feb. 27, 2003", 9 pgs.

"U.S. Appl. No. 09/339,071, Preliminary Amendment filed Sep. 25, 2006", 11 pgs.

"U.S. Appl. No. 09/339,071, Preliminary Amendment filed Oct. 16, 2007", 10 pgs.

"U.S. Appl. No. 09/339,071, Response filed Feb. 15, 2008 to Non Final Office Action mailed Nov. 15, 2007", 5 pgs.

"U.S. Appl. No. 09/339,071, Response filed Apr. 15, 2004 to Final Office Action mailed Jan. 28, 2004", 8 pgs.

"U.S. Appl. No. 09/339,071, Response filed Apr. 16, 2007 to Non Final Office Action mailed Oct. 12, 2006", 11 pgs.

"U.S. Appl. No. 09/339,071, Response filed May 23, 2006 to Final Office Action mailed Jan. 25, 2006", 14 pgs.

"U.S. Appl. No. 09/339,071, Response filed Jun. 17, 2002 to Non Final Office Action mailed Dec. 17, 2001", 7 pgs.

"U.S. Appl. No. 09/339,071, Response filed Jun. 28, 2005 to Final Office Action mailed Dec. 15, 2004", 15 pgs.

"U.S. Appl. No. 09/339,071, Response filed Jul. 3, 2000 to Restriction Requirement mailed Jun. 9, 2000", 2 pgs.

"U.S. Appl. No. 09/339,071, Response filed Sep. 24, 2004 to Non Final Office Action mailed Jun. 24, 2004", 11 pgs.

"U.S. Appl. No. 09/339,071, Response filed Nov. 2, 2005 to Non Final Office Action mailed Aug. 2, 2005", 12 pgs.

"U.S. Appl. No. 09/339,071, Response filed Nov. 21, 2003 to Non Final Office Action mailed May 21, 2003", 11 pgs.

"U.S. Appl. No. 09/339,071, Restriction Requirement mailed Jun. 9, 2000", 8 pgs.

"U.S. Appl. No. 09/382,433, Amendment filed Jan. 23, 2003 in Response to Non-Final Office Action mailed Jul. 23, 2002", 8 pgs.

"U.S. Appl. No. 09/382,433, Amendment filed Jun. 4, 2001 in Response to Non-Final Office Action mailed Feb. 28, 2001", 5 pgs.

"U.S. Appl. No. 09/382,433, Amendment filed Jun. 18, 2002 in Response to Office Action mailed Jun. 3, 2002", 2 pgs.

"U.S. Appl. No. 09/382,433, Amendment filed Jul. 23, 2004 in Response to Non-Final Office Action mailed Jan. 28, 2004", 11 pgs.

"U.S. Appl. No. 09/382,433, Amendment filed Oct. 13, 2003 in Response to Non-Final Office Action mailed Apr. 11, 2003", 11 pgs.

"U.S. Appl. No. 09/382,433, Amendment filed Nov. 30, 2000 in Response to Office Action mailed Nov. 20, 2000", 2 pgs.

"U.S. Appl. No. 09/382,433, Final Office Action mailed Aug. 24, 2001", 7 pgs.

"U.S. Appl. No. 09/382,433, Non-Final Office Action mailed Jan. 28, 2004", 9 pgs.

"U.S. Appl. No. 09/382,433, Non-Final Office Action mailed Feb. 28, 2001", 7 pgs.

"U.S. Appl. No. 09/382,433, Non-Final Offlce Action mailed Apr. 11, 2003", 13 pgs.

"U.S. Appl. No. 09/382,433, Non-Final Office Action mailed Jul. 23, 2002", 5 pgs.

"U.S. Appl. No. 09/382,433, Notice of Allowance mailed Sep. 8, 2004", 5 pgs.

"U.S. Appl. No. 09/382,433, Office Action mailed Jun. 3, 2002", 4 pgs.

"U.S. Appl. No. 09/382,433, Preliminary Amendment filed Feb. 25, 2002 in Response to Final Office Action mailed Aug. 24, 2001", 7 pgs.

"U.S. Appl. No. 09/416,192, Final Office Action mailed Jul. 2, 2002", 4 pgs.

"U.S. Appl. No. 09/416,192, Final Office Action mailed Nov. 18, 2003", 5 pgs.

(56) References Cited

OTHER PUBLICATIONS

"U.S. Appl. No. 09/416,192, Non Final Office Action mailed Mar. 7, 2003", 4 pgs.

"U.S. Appl. No. 09/416,192, Non Final Office Action mailed Jul. 19, 2001", 4 pgs.

"U.S. Appl. No. 09/416,192, Notice of Allowance mailed May 14, 2004", 5 pgs.

"U.S. Appl. No. 09/416,192, Response filed Jan. 2, 2003 to Final Office Action mailed Jul. 2, 2002", 3 pgs.

"U.S. Appl. No. 09/416,192, Response filed Jan. 17, 2002 to Non Final Office Action mailed Jul. 19, 2001", 4 pgs.

"U.S. Appl. No. 09/416,192, Response filed Feb. 18, 2004 to Final Office Action mailed Nov. 18, 2003", 5 pgs.

"U.S. Appl. No. 09/416,192, Response filed May 1, 2001 to Restriction Requirement mailed Mar. 27, 2001", 6 pgs.

"U.S. Appl. No. 09/416,192, Response filed Sep. 8, 2003 to Non Final Office Action mailed Mar. 7, 2003", 3 pgs.

"U.S. Appl. No. 09/968,595, Advisory Action mailed Mar. 30, 2007", 3 pgs.

"U.S. Appl. No. 09/968,595, Examiner Interview Summary filed Jul. 18, 2006", 3 pgs.

"U.S. Appl. No. 09/968,595, Examiner Interview Summary mailed Oct. 10, 2008", 2 pgs.

"U.S. Appl. No. 09/968,595, Examiner Interview Summary mailed Nov. 17, 2009", 3 pgs.

"U.S. Appl. No. 09/968,595, Final Office Action mailed Jan. 8, 2007", 16 pgs.

"U.S. Appl. No. 09/968,595, Final Office Action mailed Feb. 11, 2008", 14 pgs.

"U.S. Appl. No. 09/968,595, Final Office Action mailed May 11, 2010", 22 pgs.

"U.S. Appl. No. 09/968,595, Non Final Office Action mailed Mar. 23, 2006", 12 pgs.

"U.S. Appl. No. 09/968,595, Non Final Office action mailed Jun. 3, 2009", 14 pgs.

"U.S. Appl. No. 09/968,595, Non Final Office Action mailed Jun. 18, 2007", 18 pgs.

"U.S. Appl. No. 09/968,595, Non Final Office Action mailed Jun. 27, 2008", 15 pgs.

"U.S. Appl. No. 09/968,595, Non Final Office Action mailed Aug. 16, 2010", 27 pgs.

"U.S. Appl. No. 09/968,595, Non Final Office Action mailed Oct. 26, 2009", 16 pgs.

"U.S. Appl. No. 09/968,595, Preliminary Amendment filed Feb. 17, 2006", 6 pgs.

"U.S. Appl. No. 09/968,595, Preliminary Amendment filed Apr. 3, 2007", 13 pgs.

"U.S. Appl. No. 09/968,595, Response filed Jan. 26, 2010 to Non Final Office Action mailed Oct. 26, 2009", 1 pg.

"U.S. Appl. No. 09/968,595, Response filed Mar. 7, 2007 to Final Office Action mailed Jan. 8, 2007", 2 pgs.

"U.S. Appl. No. 09/968,595, Response filed Apr. 11, 2008 to Final Office Action mailed Feb. 11, 2008", 10 pgs.

"U.S. Appl. No. 09/968,595, Response filed Jul. 5, 2006 to Non Final Office Action mailed Mar. 23, 2006", 14 pgs.

"U.S. Appl. No. 09/968,595, Response filed Jul. 12, 2010 to Final Office Action mailed May 11, 2010", 14 pgs.

"U.S. Appl. No. 09/968,595, Response filed Jul. 30, 2009 to Non Final Office Action mailed Jun. 3, 2009", 12 pgs.

"U.S. Appl. No. 09/968,595, Response filed Sep. 26, 2008 to Non Final Office Action mailed Jun. 27, 2008", 9 pgs.

"U.S. Appl. No. 09/968,595, Response filed Oct. 4, 2007 to Non Final Office Action mailed Jun. 18, 2007", 2 pgs.

"U.S. Appl. No. 09/968,595, Response filed Oct. 12, 2006 to Non Final Office Action mailed Oct. 6, 2006", 2 pgs.

"U.S. Appl. No. 09/968,595, Supplemental Response to Non Final Office Action mailed Jun. 27, 2008", 11 pgs.

"U.S. Appl. No. 10/403,650, Advisory Action mailed Mar. 15, 2010", 4 pgs.

"U.S. Appl. No. 10/403,650, Advisory Action mailed Sep. 17, 2008", 3 pgs.

"U.S. Appl. No. 10/403,650, Advisory Action mailed Oct. 2, 2009", 3 pgs.

"U.S. Appl. No. 10/403,650, Examiner Interview Summary filed Oct. 20, 2009", 2 pgs.

"U.S. Appl. No. 10/403,650, Final Office Action mailed Jun. 24, 2009", 7 pgs.

"U.S. Appl. No. 10/403,650, Final Office Action mailed Jun. 27, 2008", 9 pgs.

"U.S. Appl. No. 10/403,650, Final Office Action mailed Oct. 17, 2007", 7 pgs.

"U.S. Appl. No. 10/403,650, Final Office Action mailed Nov. 25, 2009", 7 pgs.

"U.S. Appl. No. 10/403,650, Non Final Office Action mailed Apr. 12, 2007", 11 pgs.

"U.S. Appl. No. 10/403,650, Non Final Office Action mailed Nov. 15, 2005", 5 pgs.

"U.S. Appl. No. 10/403,650, Non Final Office Action mailed Nov. 26, 2007", 8 pgs.

"U.S. Appl. No. 10/403,650, Non Final Office Action mailed Dec. 24, 2008", 8 pgs.

"U.S. Appl. No. 10/403,650, Preliminary Amendment filed Feb. 26, 2008", 10 pgs.

"U.S. Appl. No. 10/403,650, Preliminary Amendment filed Sep. 22, 2008", 10 pgs.

"U.S. Appl. No. 10/403,650, Preliminary Amendment filed Oct. 30, 2007", 9 pgs.

"U.S. Appl. No. 10/403,650, Response filed Jan. 25, 2010 to Final Office Action mailed Nov. 25, 2009", 10 pgs.

"U.S. Appl. No. 10/403,650, Response filed Feb. 15, 2006 to Non final Office Action mailed Nov. 15, 2005", 9 pgs.

"U.S. Appl. No. 10/403,650, Response filed Mar. 24, 2009 to Non Final office Action mailed Dec. 24, 2008", 9 pgs.

"U.S. Appl. No. 10/403,650, Response filed Jul. 28, 2005 to Restriction Requirement mailed Jul. 12, 2005", 2 pgs.

"U.S. Appl. No. 10/403,650, Response filed Aug. 10, 2007 to Non final Office Action mailed Apr. 12, 2007", 11 pgs.

"U.S. Appl. No. 10/403,650, Response filed Aug. 24, 2009 to Non final Office Action mailed Jun. 24, 2009", 11 pgs.

"U.S. Appl. No. 10/403,650, Response filed Aug. 25, 2008 to Final Office Action mailed Jun. 27, 2008", 10 pgs.

"U.S. Appl. No. 10/819,092, Final Office Action mailed Jan. 9, 2008", 11 pgs.

"U.S. Appl. No. 10/819,092, Final Office Action mailed Mar. 13, 2009", 11 pgs.

"U.S. Appl. No. 10/819,092, Final Office Action mailed Sep. 28, 2009", 13 pgs.

"U.S. Appl. No. 10/819,092, Non Final Office Action mailed Sep. 3, 2008", 11 pgs.

"U.S. Appl. No. 10/819,092, Preliminary Amendment filed Jul. 10, 2009 to Final Office Action mailed Mar. 13, 2009", 9 pgs.

"U.S. Appl. No. 10/819,092, Response filed Mar. 10, 2008 to Final Office Action mailed Jan. 9, 2008", 10 pgs.

"U.S. Appl. No. 10/819,092, Response filed Jun. 9, 2008 to Restriction Requirement mailed May 12, 2008", 6 pgs.

"U.S. Appl. No. 10/819,092, Response filed Dec. 3, 2008 to Non Final Office Action mailed Sep. 3, 2008", 8 pgs.

"U.S. Appl. No. 10/845,400, Response filed Dec. 22, 2010 to Non Final Office mailed Jun. 22, 2010", 7 pgs.

"U.S. Appl. No. 10/854,400 , Response filed Jan. 11, 2012 to Non Final Office Action mailed Oct. 11, 2011", 7 pgs.

"U.S. Appl. No. 10/854,400 , Response filed Apr. 29, 2013 to Non Final Office Action mailed Jan. 31, 2013", 11 pgs.

"U.S. Appl. No. 10/854,400, Advisory Action mailed Apr. 6, 2010", 2 pgs.

"U.S. Appl. No. 10/854,400, Decision on Pre-Appeal Brief Request mailed Oct. 23, 2012", 2 pgs.

"U.S. Appl. No. 10/854,400, Examiner Interview Summary mailed Apr. 15, 2013", 3 pgs.

"U.S. Appl. No. 10/854,400, Final Office Action mailed Jan. 19, 2010", 11 pgs.

(56) References Cited

OTHER PUBLICATIONS

"U.S. Appl. No. 10/854,400, Final Office Action mailed Mar. 14, 2011", 11 pgs.
"U.S. Appl. No. 10/854,400, Non Final Office Action mailed Jan. 31, 2013", 14 pgs.
"U.S. Appl. No. 10/854,400, Non Final Office Action mailed Jun. 22, 2010", 10 pgs.
"U.S. Appl. No. 10/854,400, Non Final Office Action mailed Jul. 9, 2009", 12 pgs.
"U.S. Appl. No. 10/854,400, Non Final Office Action mailed Oct. 11, 2011", 9 pgs.
"U.S. Appl. No. 10/854,400, Pre-Appeal Brief Request filed Sep. 24, 2012", 5 pgs.
"U.S. Appl. No. 10/854,400, Preliminary Amendment filed May 26, 2004", 2 pgs.
"U.S. Appl. No. 10/854,400, Response filed Mar. 23, 2010 to Final Office Action mailed Jan. 19, 2010", 6 pgs.
"U.S. Appl. No. 10/854,400, Response filed Jul. 14, 2011 to Final Office Action mailed Mar. 14, 2011", 7 pgs.
"U.S. Appl. No. 10/854,400, Response filed Oct. 2, 2009 to Non Final Office Action mailed Jul. 9, 2009", 13 pgs.
"U.S. Appl. No. 10/997,737, Advisory Action mailed Aug. 29, 2008", 3 pgs.
"U.S. Appl. No. 10/997,737, Advisory Action mailed Dec. 5, 2006", 3 pgs.
"U.S. Appl. No. 10/997,737, Amendment filed Jun. 8, 2009 in Response to Non Final Office Action mailed Mar. 16, 2009", 12 pgs.
"U.S. Appl. No. 10/997,737, Examiner Interview Summary mailed Jan. 19, 2010", 2 pgs.
"U.S. Appl. No. 10/997,737, Examiner Interview Summary mailed Oct. 31, 2007", 2 pgs.
"U.S. Appl. No. 10/997,737, Final Office Action mailed Feb. 20, 2008", 10 pgs.
"U.S. Appl. No. 10/997,737, Final Office Action mailed Jun. 10, 2008", 11 pgs.
"U.S. Appl. No. 10/997,737, Final Office Action mailed Oct. 24, 2006", 6 pgs.
"U.S. Appl. No. 10/997,737, Non Final Office Action mailed Mar. 16, 2009", 7 pgs.
"U.S. Appl. No. 10/997,737, Non Final Office Action mailed Jun. 27, 2006", 12 pgs.
"U.S. Appl. No. 10/997,737, Non Final Office Action mailed Oct. 29, 2008", 8 pgs.
"U.S. Appl. No. 10/997,737, Preliminary Amendment filed Feb. 21, 2007", 9 pgs.
"U.S. Appl. No. 10/997,737, Preliminary Amendment filed Nov. 24, 2004", 3 pgs.
"U.S. Appl. No. 10/997,737, Response filed Jan. 11, 2008 to Non Final Office Action mailed Jul. 24, 2007", 14 pgs.
"U.S. Appl. No. 10/997,737, Response filed Apr. 4, 2008 to Final Office Action mailed Feb. 20, 2008", 11 pgs.
"U.S. Appl. No. 10/997,737, Response filed Jun. 13, 2008 to Final Office Action mailed Jun. 10, 2008", 11 pgs.
"U.S. Appl. No. 10/997,737, Response filed Sep. 10, 2009 to Non Final Office Action mailed Mar. 16, 2009", 15 pgs.
"U.S. Appl. No. 10/997,737, Response filed Sep. 27, 2006 to Non Final Office Action mailed Jun. 27, 2006", 7 pgs.
"U.S. Appl. No. 10/997,737, Response filed Oct. 17, 2007 to Restriction Requirement mailed Jul. 24, 2007", 14 pgs.
"U.S. Appl. No. 10/997,737, Response filed Nov. 10, 2006 to Final Office Action mailed Oct. 24, 2006", 10 pgs.
"U.S. Appl. No. 10/997,737, Response filed on Dec. 12, 2008 to Non Final Office Action mailed Oct. 29, 2008", 11 pgs.
"U.S. Appl. No. 10/997,737, Restriction Requirement mailed Jul. 24, 2007", 10 pgs.
"U.S. Appl. No. 11/017,593, Final Office Action mailed Sep. 6, 2006", 10 pgs.
"U.S. Appl. No. 11/017,593, Non Final Office Action mailed Sep. 7, 2005", 7 pgs.
"U.S. Appl. No. 11/017,593, Response filed Feb. 7, 2006 to Non Final Office Action mailed Sep. 7, 2005", 11 pgs.
"U.S. Appl. No. 11/017,593, Response filed May 12, 2006 to Restriction Requirement mailed Apr. 18, 2006", 7 pgs.
"U.S. Appl. No. 11/267,386, Advisory Action mailed May 22, 2009", 3 pgs.
"U.S. Appl. No. 11/267,386, Advisory Action mailed Jun. 4, 2010", 3 pgs.
"U.S. Appl. No. 11/267,386, Advisory Action mailed Jun. 16, 2009", 3 pgs.
"U.S. Appl. No. 11/267,386, Examiner Interview Summary filed Sep. 8, 2009", 2 pgs.
"U.S. Appl. No. 11/267,386, Final Office Action mailed Mar. 10, 2009", 8 pgs.
"U.S. Appl. No. 11/267,386, Final Office Action mailed Mar. 30, 2010", 11 pgs.
"U.S. Appl. No. 11/267,386, Final Office Action mailed Jul. 7, 2009", 10 pgs.
"U.S. Appl. No. 11/267,386, Final Office Action mailed Aug. 19, 2011", 13 pgs.
"U.S. Appl. No. 11/267,386, Non Final Action mailed Sep. 29, 2009", 10 pgs.
"U.S. Appl. No. 11/267,386, Non Final Office Action mailed Jun. 17, 2008", 10 pgs.
"U.S. Appl. No. 11/267,386, Non Final Office Action mailed Nov. 29, 2010", 11 pgs.
"U.S. Appl. No. 11/267,386, Notice of Allowability mailed Oct. 5, 2012", 2 pgs.
"U.S. Appl. No. 11/267,386, Notice of Allowance mailed Mar. 29, 2012", 10 pgs.
"U.S. Appl. No. 11/267,386, Preliminary Amendment filed Jun. 10, 2009", 6 pgs.
"U.S. Appl. No. 11/267,386, Response filed Jan. 18, 2012 Final Office Action mailed Aug. 19, 2011", 7 pgs.
"U.S. Appl. No. 11/267,386, Response filed May 1, 2008 to Restriction Requirement mailed Apr. 2, 2008", 6 pgs.
"U.S. Appl. No. 11/267,386, Response filed May 7, 2009 to Final Office Action mailed Mar. 10, 2009", 6 pgs.
"U.S. Appl. No. 11/267,386, Response filed May 20, 2010 to Final Office Action mailed Mar. 30, 2010", 7 pgs.
"U.S. Appl. No. 11/267,386, Response filed May 27, 2011 to Non Final Office Action mailed Nov. 29, 2010", 7 pgs.
"U.S. Appl. No. 11/267,386, Response filed May 28, 2009 to Advisory Action mailed May 22, 2009", 2 pgs.
"U.S. Appl. No. 11/267,386, Response filed Sep. 17, 2008 to Non Final Office Action mailed Jun. 17, 2008", 8 pgs.
"U.S. Appl. No. 11/267,386, Response filed Dec. 29, 2009 to Non Final Office Action mailed Sep. 29, 2009", 6 pgs.
"U.S. Appl. No. 11/267,386, Restriction Requirement mailed Apr. 2, 2003", 10 pgs.
"U.S. Appl. No. 11/267,386, Supplemental Notice of Allowability mailed May 9, 2012", 7 pgs.
"U.S. Appl. No. 11/267,386, Supplemental Notice of Allowability mailed Jul. 18, 2012", 4 pgs.
"U.S. Appl. No. 11/494,719, Advisory Action mailed Jan. 23, 2008", 3 pgs.
"U.S. Appl. No. 11/494,719, Advisory Action mailed Mar. 25, 2009", 3 pgs.
"U.S. Appl. No. 11/494,719, Examiner Interview Summary mailed Feb. 23, 2010", 3 pgs.
"U.S. Appl. No. 11/494,719, Examiner Interview Summary mailed Aug. 27, 2009", 2 pgs.
"U.S. Appl. No. 11/494,719, Final Office Action mailed Jan. 8, 2009", 7 pgs.
"U.S. Appl. No. 11/494,719, Final Office Action mailed Nov. 8, 2007", 8 pgs.
"U.S. Appl. No. 11/494,719, Final Office Action mailed Nov. 16, 2009", 8 pgs.
"U.S. Appl. No. 11/494,719, Non Final Action mailed Mar. 28, 2008", 9 pgs.
"U.S. Appl. No. 11/494,719, Non Final Office Action mailed May 30, 2007", 9 pgs.

(56) References Cited

OTHER PUBLICATIONS

"U.S. Appl. No. 11/494,719, Non Final Office Action mailed Jun. 30, 2009", 7 pgs.
"U.S. Appl. No. 11/494,719, Notice of Allowance mailed Apr. 18, 2012", 8 pgs.
"U.S. Appl. No. 11/494,719, Response filed Jan. 8, 2008 to Final Office Action mailed Nov. 8, 2007", 11 pgs.
"U.S. Appl. No. 11/494,719, Response filed Feb. 18, 2010 to Final Office Action mailed Nov. 16, 2009", 10 pgs.
"U.S. Appl. No. 11/494,719, Response filed Mar. 9, 2009 to Final Office Action mailed Jan. 8, 2009", 9 pgs.
"U.S. Appl. No. 11/494,719, Response filed Jun. 25, 2008 to Non Final Office Action mailed Mar. 28, 2008", 13 pgs.
"U.S. Appl. No. 11/494,719, Response filed Aug. 30, 2007 to Non Final Office Action mailed May 30, 2007", 2 pgs.
"U.S. Appl. No. 11/494,719, Response filed Sep. 1, 2009 to Non Final Office Action mailed Jun. 30, 2009", 10 pgs.
"U.S. Appl. No. 11/494,719, Response filed Oct. 13, 2008 to Restriction Requirement mailed Sep. 12, 2008", 6 pgs.
"U.S. Appl. No. 11/494,719, Restriction Requirement mailed Sep. 12, 2008", 7 pgs.
"U.S. Appl. No. 11/714,669, Final Office Action mailed Aug. 12, 2009", 8 pgs.
"U.S. Appl. No. 11/714,669, Final Office Action mailed Sep. 13, 2011", 11 pgs.
"U.S. Appl. No. 11/714,669, Non Final Office Action mailed May 13, 2010", 6 pgs.
"U.S. Appl. No. 11/714,669, Non Final Office Action mailed Aug. 1, 2008", 8 pgs.
"U.S. Appl. No. 11/714,669, Non Final Office Action mailed Nov. 9, 2010", 9 pgs.
"U.S. Appl. No. 11/714,669, Non Final Office Action mailed Nov. 13, 2009", 6 pgs.
"U.S. Appl. No. 11/714,669, Response filed Jan. 12, 2012 to Final Office Action mailed Sep. 13, 2011", 8 pgs.
"U.S. Appl. No. 11/714,669, Response filed May 9, 2011 to Non Final Office Action mailed Nov. 9, 2010", 8 pgs.
"U.S. Appl. No. 11/714,669, Response filed Jul. 1, 2010 to Non Final Office Action mailed Nov. 13, 2009", 8 pgs.
"U.S. Appl. No. 11/714,669, Response filed Oct. 13, 2009 to Final Office Action mailed Aug. 12, 2009", 7 pgs.
"U.S. Appl. No. 11/714,669, Response filed Nov. 3, 2008 to Non Final Office Action mailed Aug. 1, 2008", 8 pgs.
"U.S. Appl. No. 11/714,669, Response filed Dec. 14, 2009 to Non Final Office Action mailed Nov. 13, 2009", 6 pgs.
"U.S. Appl. No. 12/689,568, Final Office Action mailed Apr. 25, 2012", 8 pgs.
"U.S. Appl. No. 12/689,568, Final Office Action mailed Dec. 20, 2012", 20 pgs.
"U.S. Appl. No. 12/689,568, Non Final Office Action mailed Sep. 8, 2011", 22 pgs.
"U.S. Appl. No. 12/689,568, Pre-Appeal Brief Request filed Sep. 25, 2012", 5 pgs.
"U.S. Appl. No. 12/689,568, Preliminary Amendment filed Jan. 19, 2010", 5 pgs.
"U.S. Appl. No. 12/689,568, Response filed Feb. 8, 1212 to Non Final Office Action mailed Sep. 8, 2011", 11 pgs.
"U.S. Appl. No. 12/689,568, Response filed Jun. 29, 2011 to Restriction Requirement mailed May 31, 2011", 8 pgs.
"U.S. Appl. No. 12/689,568, Restriction Requirement mailed May 31, 2011", 7 pgs.
"U.S. Appl. No. 13/184,289, Final Office Action mailed Dec. 7, 2012", 22 pgs.
"U.S. Appl. No. 13/184,289, Non Final Office Action mailed Jun. 8, 2012", 15 pgs.
"U.S. Appl. No. 13/184,289, Preliminary Amendment filed Jan. 20, 2012", 8 pgs.
"U.S. Appl. No. 13/184,289, Response filed Nov. 5, 2012 to Non Final Office Action mailed Jun. 8, 2012", 13 pgs.
"U.S. Appl. No. 10/854,400, Final Office Action mailed May 24, 2012", 9 pgs.
"U.S. Appl. No. 13/184,289, Pre-Appeal Brief Request filed Mar. 6, 2013", 4 pgs.
"Chinese Application Serial No. 99812468.0, First Office Action issued Jul. 25, 2003", (w/ English Translation), 10 pgs.
*Clinical Biomechanics of the Spine*, 2nd Edition, (1990), p. 482.
"European Application Serial No. 05822048, Supplementary European Search Report mailed Mar. 5, 2009", 6 pgs.
"European Application Serial No. 05822048.4, Supplementary European Search Report mailed Mar. 24, 2009", 12 pgs.
"European Application Serial No. 96920238.1, Supplementary Partial European Search Report mailed Nov. 21, 2002", 5 pgs.
"European Application Serial No. 98915149.3, Supplementary Partial European Search Report mailed Jul. 11, 2003", 5 pgs.
"European Application Serial No. 93915149.3, Supplementary Partial European Search Report mailed Apr. 1, 2003", 5 pgs.
"European Application Serial No. 99966681.1, Office Action mailed Jan. 9, 2009", 5 pgs.
"European Application Serial No. 99966681.1, Office Action mailed Feb. 7, 2006", 5 pgs.
"European Application Serial No. 99966681.1, Office Action mailed Mar. 11, 2005", 3 pgs.
"European Application Serial No. 99966681.1, Office Action mailed Sep. 11, 2007", 5 pgs.
"European Application Serial No. 99966681.1, Reply filed Apr. 14, 2008 to Office Action mailed Sep. 11, 2007", 7 pgs.
"European Application Serial No. 99966681.1, Reply filed Jun. 19, 2006 to Office Action mailed Feb. 7, 2006", 11 pgs.
"European Application Serial No. 99966681.1, Response filed Jul. 21, 2005 to Office Action mailed Mar. 11, 2005", 3 pgs.
"European Application Serial No, 99966681,1, Response filed Jul. 23, 2004 to Partial European Search Report mailed Jun. 14, 2004", 4 pgs.
"European Application Serial No. 99966631.1, Supplementary Partial European Search Report mailed Jun. 14, 2004", 6 pgs.
"European Application Serial No. 99966681.1, Supplementary Search Report mailed Sep. 8, 2004", 6 pgs.
"International Application Serial No. PCT/US00/15888, International Preliminary Examination Report mailed Jul. 23, 2001", 43 pgs.
"International Application Serial No. PCT/US00/15888, International Search Report mailed Aug. 21, 2000", 2 pgs.
"International Application Serial No. PCT/US00/16859, International Preliminary Examination Report mailed Dec. 2, 2002", 8 pgs.
"International Application Serial No. PCT/US00/16859, International Search Report mailed Oct. 16, 2000", 7 pgs.
"International Application Serial No. PCT/US00/16859, Written Opinion mailed Oct. 19, 2001", 6 pgs.
"International Application Serial No. PCT/US00/26990, International Preliminary Examination Report mailed Oct. 24, 2001", 4 pgs.
"International Application Serial No. PCT/US00/26990, International Search Report mailed Dec. 27, 2000", 3 pgs.
"International Application Serial No. PCT/US05/41021, International Search Report mailed Jan. 25, 2007", 1 pg.
"International Application Serial No. PCT/US05/41021, Written Opinion mailed Jan. 25, 2007", 3 pgs.
"International Application Serial No. PCT/US05/41339, International Search Report and Written Opinion mailed Jun. 20, 2006", 9 pgs.
"International Application Serial No. PCT/US2005/41339, Written Opinion mailed Jun. 20, 2006", 3 pgs.
"International Application Serial No. PCT/US2005/41339, Written Opinion mailed Jun. 20, 2006", 6 pgs.
"International Application Serial No. PCT/US96/07047, International Preliminary Examination Report mailed Sep. 4, 1997", 5 pgs.
"International Application Serial No. PCT/US96/07047, International Search Report mailed Oct. 2, 1996", 7 pgs.
"International Application Serial No. PCT/US96/07047, Written Opinion mailed May 22, 1997", 4 pgs.
"International Application Serial No. PCT/US98/05600, International Preliminary Examination Report mailed Jun. 16, 1999", 7 pgs.
"International Application Serial No. PCT/US98/05600, International Search Report mailed Jul. 9, 1998", 6 pgs.

(56) References Cited

OTHER PUBLICATIONS

"International Application Serial No. PCT/US98/05600, Written Opinion mailed Jan. 27, 1999", 6 pgs.
"International Application Serial No. PCT/US99/19935, Article 34 Amendment filed Nov. 17, 2000", 19 pgs.
"International Application Serial No. PCT/U899/19935, International Preliminary Examination Report mailed Feb. 26, 2001", 23 pgs.
"International Application Serial No. PCT/US99/19935, International Search Report mailed Mar. 24, 2000", 6 pgs.
"International Application Serial No. PCT/US99/19935, Written Opinion mailed Sep. 19, 2000", 7 pgs.
"International Application Serial No. PCT/US99/31030, International Preliminary Examination Report mailed Jun. 12, 2001", 8 pgs.
"International Application Serial No. PCT/US99/31030, International Search Report Jul. 13, 2000", 5 pgs.
"International Application Serial No. PCT/US99/31030, Written Opinion mailed Dec. 13, 2000", 7 pgs.
"Japanese Application Serial No. 2000-567165, Office Action mailed Apr. 9, 2009", (English Translation), 3 pgs.
"Japanese Application Serial No. 2000-591930, Argument and Amendment filed Feb. 26, 2008 filed in Response to Office Action mailed Nov. 27, 2007", 4 pgs.
"Japanese Application Serial No. 2000-591930, Decision of Refusal mailed Mar. 25, 2008", (w/ English Translation), 3 pgs.
"Japanese Application Serial No. 2000-591930, Official Action mailed Nov. 27, 2007", (English Translation), 3 pgs.
"Japanese Application Serial No. 545857/98, Amendment and Argument filed Jan. 9, 2007", 11 pgs.
"Japanese Application Serial No. 545857/98, Appeal Brief and Amendment filed Jun. 25, 2007", 10 pgs.
"Japanese Application Serial No. 545857/98, Final Rejection mailed Mar. 26, 2007", (English Translation), 2 pgs.
"Japanese Application Serial No. 545857/98, Office Action mailed Aug. 17, 2006", (English Translation), 6 pgs.
"Machine Translation of JP 58-109212, published Jul. 25, 1983", 24 pgs.
"Put Your Patient's Recovery Steps Ahead with the Sutter CPM 9000", Sutter Biomedical Inc., *SUT 133, V85*, (Jan. 1985), 1-6.
"Thera-Kinetics Product Literature", (1994), 26 pgs.
Allington, R, et al. "Strengthening Techniques of the Quadriceps Muscles: An Electromyographic Evaluation", *Journal of the American Therapy Association* vol. 66, No. 11, (1966), 1173-1176.
Antich, T. J., et al., "Modification of Quadriceps Femoris Muscle Exercises During Knee Rehabilitation", *Physical Therapy*, 66(8), (1986), 1246-1251.
Baumeister, T., et al., *Standard Handbook for Mechanical Engineers*, 8th Ed., McGraw-Hill Book Company, New York, NY, (1978), p. 16-8.
Biering-Sorenson, F., "A One-Year Prospective Study of Low Back Trouble in a General Population", *Danish Medical Bulletin*, 31(5), (Oct. 1984), 362-375.
During, J., et al., "Toward Standards for Posture—Postural Characteristics of the Lower Back System in Normal and Pathologic Conditions", *Spine*, 10(1), (1985), 83-87.
Elnagger, I. M., et al., "Effects of Spinal Flexion and Extension Exercises on Low-Back Pain and Spinal Mobility in Chronic Mechanical Low-Back Pain Patients", *Spine*, 16(8), (1991), 967-972.
Gough, J, et al., "An Investigation Into the Effectiveness of Various Forms of Quadriceps Exercises", *Physiotherapy*, 57(8)., (1971), 356-361.
Haberichter, P. A., et al., "Muscle Pressure Effects on Motorneuron Excitability", (Abstract R-224), *Physical Therapy*, 65(5), (1985), p. 723.
Hapgood, F., "Let Your Fingers Do the Talking", *INC—Magazine for Growing Companies*, 19(17), (Nov. 18, 1997), 119-120.
Henry, F. M., et al., "Relationships Between Individual is Strength, Speed, and Mass in an Arm Movement", *The Research Quarterly* 31(1), (1989), 24-33.

Ibrahim, A., "Communicating in real-time on-line", *New Straits Times*, Kuala Lumpar, (Nov. 6, 1997), 5 pgs.
Kishino, N. D., et al., "Quantification of Lumbar Function—Part 4: Isometric and Isokinetic Lifting Simulation in Normal Subjects and Low-Back Dysfunction Patients", *Spine*, 10(10), (1985), 921-927.
Knapik, J., et al., "Angular Specificity and Test Mode Specificity of Isometric and Isokinetic Strength Testing", *The Journal of Orthopedic and Sports Physical Therapy*, 5(2), (1983), 58-65.
Krebs, D., et al., "Knee Joing Angle: Its Relationship to Quadriceps Femoris Activity in Normal and Postarthrotomy Limbs", *Arch Phys Med. Rehabil.*, vol. 64, (1983), 441-447.
Lieb, F. J. et al., "Quadriceps Function—An Electromyographic Study Under Isometric Conditions", *The Journal of Bone and Joint Surgery*, vol. 53-A(4), (1971), 749-758.
Lindh, M., "Increase of Muscle Strength From Isomeric Quadriceps Exercises at Different knee Angles", *Scand J Rehab Med.*, II(1), (1979), 33-36.
Mayer, T. G, et al., "A prospective short-term study of chronic low back pain patients utilizing novel objective functional measurement", *Pain*, 25(1), (Apr. 1986), 53-68.
Mayer, T. G., et al., "Quantification of Lumbar Function—Part 2: Sagittal Plane Trunk Strength in Chronic Low-Back Pain Patients", *Spine*, 10(8), (1985), 765-772.
Million, R., et al., "Assessment of the progress of the back-pain patient 1981 Volvo Award in Clinical Science", *Spine*, 7(3), (May-Jun. 1982), 204-212.
Pollock, M. L., et al., "Chapter 22—Muscle", *In: Rehabiliation of the Spine: Science and Practice*, Hochschuler, S., et al., Editors, Mosby-Year Book, Inc., (1993), 263-284.
Rasch, P. J., "Progressive Resistance Exercise: Isotonic and Isometric: A Review", The *Journal of the Association for Physical and Mental Rehabilitation*, 15(2), (1961), 46-50.
Sikorski, J. M., et al., "A Rationalized Approach to Physiotherapy for Low-Back Pain", *Spine*, 10(6), (1985), 571-579.
Skurja, Jr., M., et al., "Quadriceps Action in Straight Leg Raise Versus Isolated Knee Extension", EMG and Tension Study, *Physical Therapy*, 60, (1980), p. 582.
Smidt, G., et al., "Assessment of Abdominal and Back Extensor Function—A Quantitative Approach and Results for Chronic Low-Back Patients", *Spine*, 8(2), (1983), 211-219.
Soderberg, G. L., et al., "An Electromyographic Analysis of Quadriceps Femoris Muscle Setting and Straight Leg Raising", *Physical Therapy*, 63(9), (1983), 1434-1438.
Soderberg, G. L., et al., "Electromyographic Analysis of Knee Exercises in Healthy Subjects and in Patients with Knee Pathologies", *Physical Therapy*, 67(11), (1987), 1691-1696.
Stratford, P., "Electromyography of the Quadriceps Femoris Muscles in Subjects with Normal Knees", *Physical Therapy*, 62(3), (1981), 279-283.
Wild, J. J., et al., "Patellar Pain and Quadriceps Rehabilitation—An EMG Study", The *American Journal of Sports Medicine*, 10(1), (1982), 12-15.
"U.S. Appl. No. 10/854,400, Final Office Action mailed Aug. 20, 2013", 13 pgs.
"U.S. Appl. No. 11/494,719, Notice of Allowance mailed May 29, 2013", 9 pgs.
"U.S. Appl. No. 11/714,669 , Response filed Oct. 7, 2013 to Non Final Office Action mailed Jun. 7, 2013", 9 pgs.
"U.S. Appl. No. 11/714,669, Non Final Office Action mailed Jun. 7, 2013", 10 pgs.
"U.S. Appl. No. 11/714,669, Notice of Allowance mailed Nov. 5, 2013", 10 pgs.
"U.S. Appl. No. 12/689,568, Non Final Office Action mailed May 23, 2013", 22 pgs.
"U.S. Appl. No. 12/689,568, Response filed Sep. 20, 2013 to Non Final Office Action mailed May 23, 2013", 10 pgs.
"U.S. Appl. No. 13/184,289 , Response filed Oct. 17, 2013 to Non Final Office Action mailed Jun. 21, 2013", 12 pgs.
"U.S. Appl. No. 13/184,289, Decision on Pre-Appeal Brief Request mailed Apr. 9, 2013", 2 pgs.
"U.S. Appl. No. 13/184,289, Examiner Interview Summary mailed Oct. 15, 2013", 2 pgs.

(56) References Cited

OTHER PUBLICATIONS

"U.S. Appl. No. 13/184,289, Non Final Office Action mailed Jun. 21, 2013", 25 pgs.

"U.S. Appl. No. 13/184,289, Response filed May 9, 2013 to Final Office Action mailed Dec. 7, 2012", 13 pgs.

"U.S. Appl. No. 13/536,660, Response filed Aug. 1, 2013 to Restriction Requirement mailed Jul. 15, 2013", 8 pgs.

"U.S. Appl. No. 13/536,660, Restriction Requirement mailed Jul. 15, 2013", 10 pgs.

"U.S. Appl. No. 10/854,400, Appeal Brief filed Dec. 19, 2013", 18 pgs.

"U.S. Appl. No. 11/714,669, Response filed Oct. 7, 2013 to Non Final Office Action mailed Jun. 7, 2013", 9 pgs.

"U.S. Appl. No. 12/689,568, Notice of Allowance mailed Nov. 27, 2013", 20 pgs.

"U.S. Appl. No. 13/184,289, Response filed Oct. 17, 2013 to Non Final Office Action mailed Jun. 21, 2013", 12 pgs.

"U.S. Appl. No. 13/536,660, Notice of Allowance mailed Nov. 27, 2013", 14 pgs.

Guralnik, J. M., et al., "A Short Physical Performance Battery Associating Lower Extremity Function: Association With Self-Reported Disability and Prediction of Mortality and Nursing Home Admission", *Journal of Gerontology: Medical Sciences*, 49(2), (1994), M85-M94.

Maxwell, T. D., et al. "Cognitive Predictors of Depression in Chronic Low Back Pain: Toward an Inclusive Model", *Journal of Behavioral Medicine*, 21(2), 131-143.

Viemero, V., et al., "Quality of Life in Individuals with Physical Disabilities", *Psychother. Psychosom.*, 67(6), (1998), 317-322.

* cited by examiner

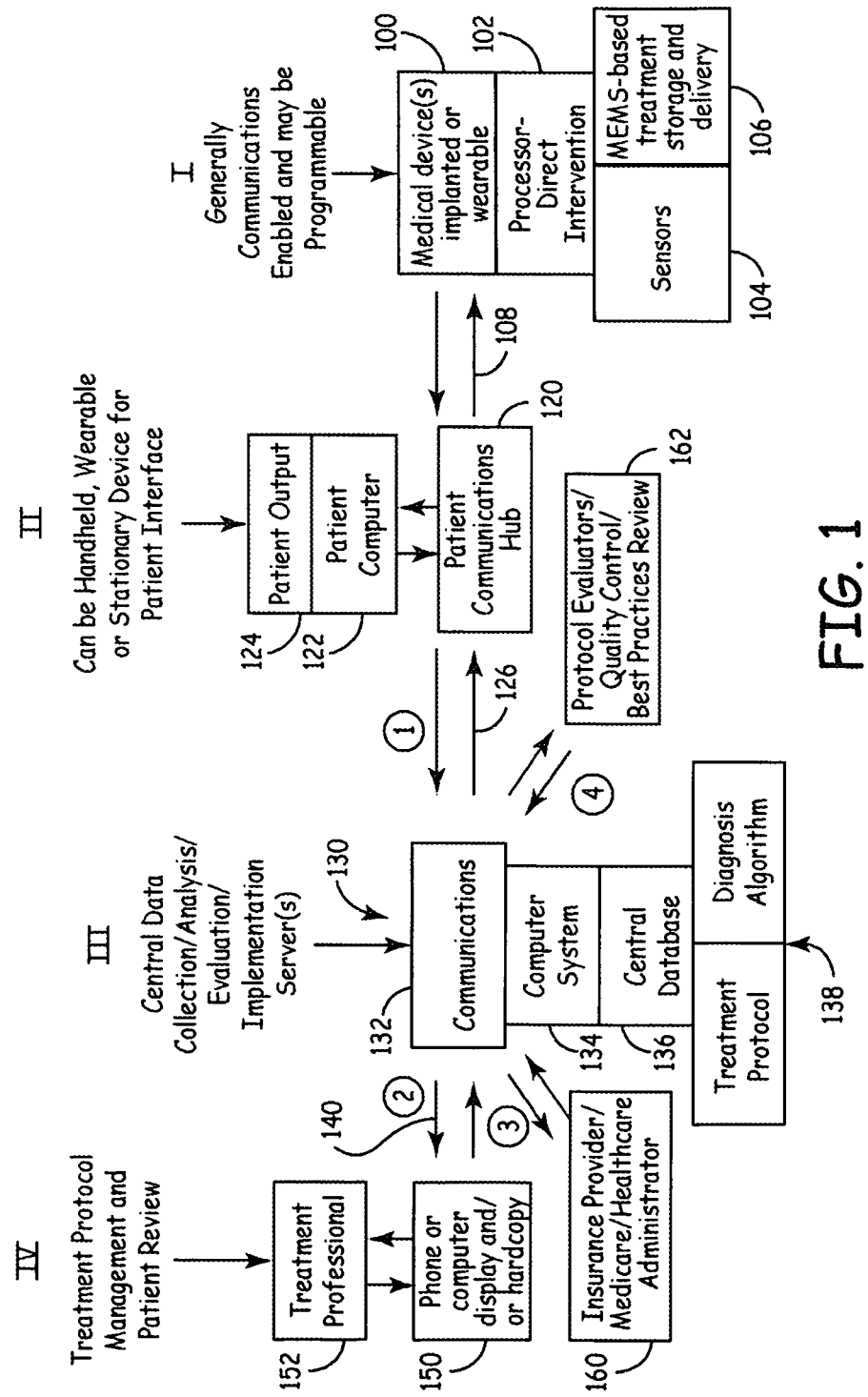

INSTRUMENTED ORTHOPEDIC AND OTHER MEDICAL IMPLANTS

CROSS REFERENCE TO RELATED APPLICATIONS

This application is a continuation of U.S. patent application Ser. No. 11/494,719, filed Jul. 27, 2006, which is a continuation of PCT application PCT/US2005/041339 to Martinson et al. filed on Nov. 15, 2005, entitled Instrumented Orthopedic and Other Medical Implants," incorporated herein by reference, which claims priority to U.S. Provisional Patent Application 60/628,050 filed on Nov. 15, 2004 to Stark et al., entitled "Instrumented Implantable Medical Devices," incorporated herein by reference and to U.S. Provisional Patent Application 60/722,361 filed on Sep. 30, 2005 to Stark et al., entitled "Instrumented Implantable Stents and Other Medical Devices," incorporated herein by reference.

FIELD OF THE INVENTION

This invention relates to medical implants, such as orthopedic implants, that are instrumented with sensors and/or treatment modalities that generally can communicate external to the patient. In some embodiments, the implants may comprise a suitable microprocessor, although other electronic analog or digital controllers can be used as an alternative to a microprocessor.

BACKGROUND OF THE INVENTION

Innovative approaches have presented considerable opportunity to revolutionize medicine through providing more automated and/or remote treatment options in a variety of contexts. The objectives are to provide improved care and accelerated treatment delivery while increasing efficiency to keep costs down. With two way communication channels, the medical professionals can be apprised of the patient's condition without an office visit and medical devices can be remotely reprogrammed or triggered.

Both muscles, bones and other tissues should be exercised or stressed to maintain strength/health. Also, bone fractures that are exposed to permissible weight bearing stress often heal more predictably and more rapidly than fractures that are not stressed at all. Improved healing based on application of appropriate stress is also believed to be true for connective tissue, such as ligaments and cartilage. Suitable stress can be applied to the tissue by the performance of selected exercises.

In particular, isometric exercises generally involves the exertion of force against an essentially immovable object. To perform isometric exercises, a restraining device can be used that has a substantially unchanging position for the duration of a particular exercise routine. Isotonic exercises involve exertion against the same weight or resistance through a range of motion. Isokinetic exercise is designed to mimic exertions that take place on a playing field or the like. When performing isokinetic exercises in a simulated environment, a machine is used to provide resistance in direct proportion to the exertion of the exerciser.

A difficulty with the application of stress to an injured tissue or combination of tissues is that the application of excessive stress can further injure the tissue rather than assist with the healing. Thus, the exercises need to be carefully planned to provide appropriate amounts of stress. Also, the performance of the exercises should be monitored closely by a physician, physical therapist or other appropriate health care professional to improve the effectiveness of the treatment and to reduce the risk of injury. The need to carefully plan and closely monitor the exercises provides a cost and motivation barrier to accessing desirable amounts of exercise.

For various injuries, disease or degeneration, implants can be used to replace or support natural structures. Thus, for example, replacement joints are commercially available to repair many faulty joints, such as the knee and hip. Also, other implants, such as pins, plates and the like can be implanted to permanently or temporarily repair or support, bone, ligaments, cartilage or the other bodily structure. In particular, various spinal cages, disc supports and the like can be used to repair spinal damage. Also, non-orthopedic tissues can be affected.

SUMMARY OF THE INVENTION

In a first aspect, the invention pertains to a biocompatible implant comprising a power source, a controller operably connected to the power source and a therapeutic energy propagating or medication delivery transducer operably connected to the controller, which can comprise a microprocessor in some embodiments. In some embodiments, the therapeutic energy propagating transducer can be an ultrasonic transmitter, a heater, a therapeutic electromagnetic transmitter, electrodes that transmits direct or alternating electrical current, an electroporous membrane or a combination thereof. A therapeutic energy propagating transducer is distinguishable in that it the propagating energy effects the associated tissue.

The power source is a battery. In additional or alternative embodiments, the power source comprises an antenna that can capture energy transmitted to the implant. The bio compatible implant can further comprise a wireless communications channel electrically connected to the microprocessor, in which the communications channel can communicate externally to a patient following implantation within a patient. In some embodiments, the wireless communications channel can transmit information from the implant and/or receive information that provides instruction to the microprocessor. The communications channel can be in communication with a central server that provides remote access to a plurality of clinicians. In some embodiments, the therapeutic energy propagating transducer comprises an infrared emitting diode, RF emitter or ultrasound emitter.

In a further aspect, the invention pertains to a biocompatible orthopedic implant comprising a support structure configured to interface with a native skeletal portion, a controller connected to the support structure, a reservoir holding a bioactive agent, and a delivery system operably connected to the controller to control the function of the delivery system. The controller may comprise a microprocessor. The delivery system can mediate release of the bioactive agent. In some embodiments, the orthopedic implant is an implantable orthopedic prosthesis, such as a replacement joint. Also, in some embodiments, the delivery system comprises a microelectromechanical structure.

In some embodiments, the bioactive agent is selected from the group consisting of an antimicrobial agent, a hormone, a cytokine, a growth factor, a hormone releasing factor, a transcription factor, an antithrombogenic agent, an antirestenosis factor, a calcium channel blocker, a blood pressure reducing agent, a pain medication, an acid, a base, a magnetic agent, a polarizing agent, a targeting agent, an imaging marker, a radioactive material, an immune active agent and combinations thereof. The bioactive agent can comprise a time released or encapsulated pharmacological agent. The delivery system can comprise a microelectromechanical structure.

The biocompatible implant can further comprise a wireless communication system operably connected to the microprocessor. In some embodiments, the communications system can be in communication with a central server that provides remote access to a plurality of clinicians. The biocompatible implant can further comprise a battery. The reservoir can be self-contained in which the reservoir is isolated from connections exterior to the body following implantation within a patient. In additional or alternative embodiments, the reservoir opens into the surroundings to deliver the biologic agent without passing through a channel longer than about 1 centimeter.

In another aspect, the invention pertains to a biocompatible implant comprising a controller, a communication system operably connected to the controller and a sensor operably connected to controller wherein the communication system can transmit values related to measurements from the sensor. The controller may comprise a microprocessor. In some embodiments, the sensor can be an accelerometer, a thermal sensor, such as a thermocouple, or a position sensor. The biocompatible implant can comprise a structure configured for attachment to bone.

In other aspects, the invention pertains to a biocompatible implant comprising a transducer, a controller comprising an integrated circuit and a radio communication device integrated with the integrated circuit. The microprocessor can be in electrical communication with the transducer. The biocompatible implant can further comprising a sensor operably connected to the controller. In some embodiments, the biocompatible implant further comprises an energy propagating transducer operably connected to the controller. The biocompatible implant may be configured for contact with a patient's skeletal system. The integrated circuit can comprise a microprocessor.

Moreover, the invention pertains to a biocompatible implant comprising a spinal fusion cage, a controller operably connected with the spinal fusion cage, a wireless communication system operably connected with the controller and a sensor operably connected to the controller and the spinal fusion cage. The controller can comprise a microprocessor. The biocompatible implant can further comprise a drug delivery device operably connected to the microprocessor to control the function of the drug delivery device.

In further aspects, the invention pertains to a biocompatible implant comprising a controller, a reservoir holding a bioactive agent, and a delivery system operably connected to the controller to control the function of the delivery system. The delivery system mediates release of the bioactive agent, and the implant is configured for implantation at or near an organ, such as an endocrine organ. The controller can comprise a microprocessor. The biocompatible implant can further comprise a communications system operably connected to the microprocessor.

In some embodiments, the invention pertains to a biocompatible implant comprising a controller, a reservoir holding a bioactive agent, and a delivery system operably connected to the controller to control the function of the delivery system. The delivery system mediates release of the bioactive agent, wherein the implant is configured for delivery of the bioactive agent into the vascular system or nervous system. The device can be configured to deliver the bio active agent into the vascular system or nervous system to target an organ.

In addition, the invention pertains to a system of implants comprising a plurality of implantable components. Each implantable component comprising a frame, a controller operably connected to the frame and a transducer operably connected to the controller and supported by the frame. The controllers of the implantable components are in communication with each other, which can be over a wired communication channel and/or a wireless communication channel. One or more controllers can comprise a microprocessor. In some embodiments, the system comprises at least one measurement transducer and at least one therapeutic transducer.

Furthermore, the invention pertains to a biocompatible implant comprising a controller, a communications system operably connected to the controller having both transmitting and receiving capability, a measurement transducer operably connected to the controller and a treatment transducer operably connected to the controller.

In other aspects, the invention pertains to a method for modifying the function of an implantable medical device. The implantable medical device comprises a controller, a communication system operably connected to the controller having both transmitting and receiving capability, a measurement transducer operably connected to the controller and a treatment transducer operably connected to the controller. The method comprises reprogramming the implantable medical device through transmitting the reprogramming information to the controller in which a new protocol is determined based on an analysis of information from the implanted medical device related to the measurements of the measurement transducer.

In additional aspects, the invention pertains to a method for operating an implanted medical device in which the method comprises transmitting from the medical device data corresponding to a condition within the patient and receiving instructions regarding the future operation of the medical device. In some embodiments, the implanted medical device communicates with a central server that comprises a best practices database and wherein the instructions from the central database to the implanted medical device are based on an evaluation of the data transmitted from the implanted device in view of best practices.

BRIEF DESCRIPTION OF THE DRAWINGS

FIG. 1 is a schematic diagram depicting the components of smart/remote medical treatment system displaying the interaction of a medical device, a patient computer, a central server/database and medical professionals.

DETAILED DESCRIPTION OF THE INVENTION

Figure 2A:
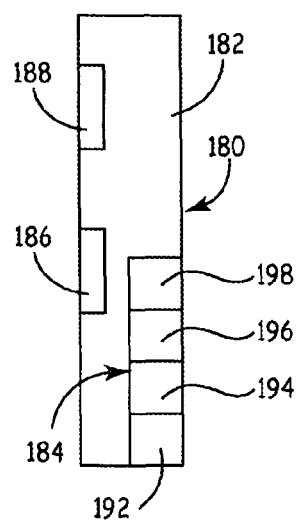
FIG. 2A is a schematic diagram of an implantable medical device.

Medical implants can incorporate sophisticated components to introduce selected functionality to the device. In some embodiments, the implant can comprise a controller, optionally comprising a microprocessor, that can be used to control the processes and/or mediate communication. Also, the smart implants can comprise a communication system that can broadcast information from the device outside of the body and in some embodiments that can receive information from outside of the body, which can be used, for example, to activate processes, deactivate processes, reprogram processes, run diagnostic programs and the like. In some embodiments, the medical implants are orthopedic implants that interface with a patient's skeletal system. The smart implantable devices can comprise one or more transducers as well as a power supply, which can be internal to the device or configured for powering through an external power source that transmits necessary power to the device within the patient. Suitable transducers can be configured to make measurements of physical, chemical or medical conditions within the patient or configured to provide a therapeutic function to the patient. Smart implants can enhance the treatment process as well as provide for efficient monitoring of the treatment process. If the device is interfaced to a remote communication system, medical professionals with the assistance of automated systems can monitor the functions remotely and provide adjustments to the protocols remotely.

Due to instrumentation of the devices, the implantable devices can provide new functionalities within an implanted device to provide corresponding improved treatment options and/or diagnostic abilities. Improved diagnostic abilities can be based on one or more measurement capabilities incorporated into the implantable device. Treatment structures can be interpreted broadly to cover structures that provide drugs or therapeutic forces to the surrounding environment within the patient. In some embodiments, microelectromechanical structures facilitate drug delivery from a stent or other small implantable structure. Furthermore, implantable power sources can be used to generate forces that are therapeutic for the neighboring tissue, although the device can be built without a power source if suitable components can be used to obtain power from sources external to the patient.

The implants described herein can be adapted for a range of suitable applications within the body. Smart stents and smart vascular grafts are described in more detail in copending U.S. patent application Ser. No. 11/267,386 to Martinson et al. filed on Nov. 4, 2005, entitled "Instrumented Implantable Stents, Vascular Grafts And Other Medical Devices," incorporated herein by reference. Also, other medical implants can be placed within a patient in muscle, a body cavity or other location. The placement of the device can be selected to be near a particular location or organ for the desired therapeutic effect. In some embodiments, the drugs are delivered at or near an endocrine organ. The size and shape of the device can be selected to be reasonably non-obtrusive for the application. Orthopedic implants as well as general implants designed for delivery for therapeutic energies are described in detail below.

In some embodiments, orthopedic implants are devices that interface within the patient with their skeletal system, i.e., bone, cartilage, tendons, and/or ligaments. The instrumented components may or may not be part of an implant that serves a mechanical function upon implantation. Some of these implantable devices are instrumented versions of devices available to repair damage or disease to the skeletal system. More specifically, suitable implants with a mechanical function include, for example, pins, screws, plates, rods, internal fixators, replacement joints, spinal cages, and the like. In other embodiments, the implant may fasten to the skeletal system to make measurements or to provide therapeutic effects without providing significant mechanical function.

The instrumentation can be inserted within the implant, for example within a sealed cavity, on the surface of the implant or a combination thereof. In some embodiments, it may be desirable to have one or more transducers at the surface of the implantable device with the remaining instrumentation within the implant. The instrumentation can be located at a plurality of locations, for example, with sensors attached to a medical implant with a mechanical function and the remaining instrumentation implanted near the medical implant with wired or wireless communication between the components of the instrumentation.

In some embodiments, the implantable device comprises a transducer. The transducer can be configured to produce electrical signals in response to conditions at the device, i.e., to make measurements within the patient, or the transducer can be configured to respond to electrical signals from an internal power source to induce a response, such as movement or direction of energy into adjacent tissue. Movement or other actuation of a transducer within the device can be used to deliver treatment such as drug delivery, to stimulate healing, accelerate revascularization, stabilize aberrant signals and/or to induce an alternative treatment function.

Transducers associated with the implant can be, for example, measurement sensors. Suitable sensors for use with an implanted device include, for example, temperature sensors, such as a thermocouple, accelerometers, strain sensors, position sensors, chemical sensors, a pressure sensor, a volume sensor, a variable resistance sensor and the like. In some embodiments, the sensors can evaluate whether or not the patient is exerting excessive forces on the healing area. Also, these sensors can monitor activity level, walking/sitting/lying status and the like. In particular, accelerometers and position sensors can evaluate if the patient is using reasonable restraint in their movements based on their injury. Use of sensors with external medical devices is described further in published PCT application WO 00/12041 to Stark et al., entitled "Orthoses for Joint Rehabilitation," and in U.S. Pat. No. 6,540,707 to Stark et al., entitled "Orthoses," both of which are incorporated herein by reference. These sensors and associated electronics can be adapted for use within implants based on the description herein. With respect to chemical sensors, suitable sensors for glucose measurements, oxygen measurements, NO measurements and other chemicals sensors can be adapted for the implants described herein. See, for example, Published PCT Application serial number WO 2005/084257A to Polcha et al., entitled "Composite Thin-Film Glucose Sensor," U.S. Pat. No. 4,815,469 to Cohen et al., entitled "Implantable Blood Oxygen Sensor and Method of Use," and Published U.S. Patent Application 2004/0176672A to Silver et al., entitled "Implantable, Retrievable, Thrombus Minimizing Sensors," which describes nitric oxide sensors, all three of which are incorporated herein by reference.

Furthermore, output transducers can be associated with the medical implant or other medical implant in addition to as an alternative to measurement transducers. The output transducers can be energy propagating transducers. Suitable energy propragating transducers can be ultrasonic transducers, such as piezoelectric elements, heaters, such as resistance heaters or infrared diodes, and/or electrodes that apply, receive or transduce a constant or pulsed current over a selected time frame. Electric currents, electromagnetic fields, ultrasound, magnetic, radio-frequency (RF), heat and/or other therapeutic energies may stimulate healing or other biological activity, such as synthesis of biological compositions, secretion of compositions and/or generation of biological electrical impulses. Energy propagating transducers are described further for external orthopedic devices, which can be adapted for implantable based on the teachings herein, in published PCT application WO 96/36278 to Stark, entitled "An Orthopedic Device Supporting Two or More Treatment Systems and Associated methods," incorporated herein by reference.

Similarly, drug delivery can be associated with an orthopedic implant. Suitable drugs include, for example, a metabolically active agent, as steroids, endocrine or pain medication, bone growth hormones, cellular cytokines and the like and combinations thereof. Suitable drug delivery systems are described in the following. Separate drug delivery units can be selectively used to deliver a particular drug based on a sensed desire for the particular drug or based on external instructions. Drug delivery can be initiated automatically, by the physician via remote controls or by the patient.

Available miniaturization approaches can be used to make very small smart devices that are controlled in some sense with a microprocessor. Similarly, communication systems can be made very small. Miniature instrumentation can be integrated directly onto the implanted medical device in some embodiments and may be integrated with a correspondingly miniature processor/controller. Small power systems are available for low power consumption applications, and auxiliary devices are available to recharge an implanted power system from outside of the body or to provide all of the power requirements to the implanted device from exterior to the patient.

In some embodiments of particular interest, it is desirable to interface the smart implantable devices with remote health care professionals to facilitate treatment and monitoring with fewer office visits. While remote monitoring can be advantageous with direct communication to health care professionals, there can be significant advantages in mediating communication through a central system, which can comprise one or more servers along with corresponding databases/distributed databases. Communication can be through radio transmission, phone transmission, satellite transmission, or the like or a combination thereof, and can be directed through the World Wide Web or corresponding Internet service, or more generally through public or secured private communications and/or networks, at some stage in the transmission process.

Automation through a central server, generally with a corresponding medical database, can be used to communicate with a large number of patients along with a large number of physicians to coordinate the treatment, outcomes monitoring, billing and other functions. Automation can also involve self-correction and/or automatic shut down and the like such that response time can be shortened to provide more effective response to changing conditions. The central server can also be used to facilitate and evaluate the fundamental selection of treatment protocols, and improve selection and/or design of treatment protocols through the analysis of a large number of treatment results to improve treatment outcomes as well as reduce costs through efficiencies. Description of medical databases and central servers is provided further in U.S. Pat. No. 6,827,670 to Stark et al., entitled "System For Medical Protocol Management" and WO 00/40171A to Oyen et al., entitled "Remote Monitoring of an Instrumented Orthosis," both of which are incorporated herein by reference. In some embodiments, the implantable devices can be reprogrammed, either by the clinician or automatically/dynamically by a processor using an appropriate algorithm, to alter their function through protocol adjustments and the like.

The improved devices described herein expand the capabilities for remote medical treatment in several dimensions. In some embodiments, therapeutic delivery is moderated by instrumentation within implantable devices, for example, based on miniature components. In additional embodiments, orthopedic implants or other medical implants can be instrumented to provide desirable monitoring functions and/or therapy management. A particular implanted medical device/system can comprise components to perform the particular functions that may be physically attached within a monolithic structure or otherwise connected, physically near each other or positioned remotely from each other to yield a desired result, in which nonattached elements may be connected physically, such as with a wire or the like, or electromagnetically for wireless communication. In some embodiments, the devices can be designed to communicate, to be controlled and/or to be powered externally using micro scale, generally radio-frequency (RF), communication systems and appropriate corresponding power systems. Communication enabled devices can be tied to appropriate communication channels for remote transmission of the measurements as well as reprogramming of the device from a remote location. The communication channel can proceed through a central database that coordinates treatment and monitoring functions for a plurality of patients and a plurality of health care professionals. Thus, the system can be used to coordinate communication and transfer of data between health care professionals, patients, insurers, regulators and others involved in the administration of health care.

More specifically, in some embodiments, the medical treatment system can have an implanted medical device optionally with its own processor and/or its own communication elements, and a local controller, for example, a personal digital assistant or the like, that can communicate with the implanted medical device as well as with a remote computer(s) connected to a suitable communication channel. Remote communication can be performed through access to a remote communication channel, for example, through a hardwire connection or through wireless communication. The remote "computer" can be a central server or set of servers that maintain a central database or a distributed database, or it can be a computer at the site of a treating health care professional. For convenience, central server refers to one or a set or servers, and central database refers to a single database or a distributed network of databases, containing a plurality of data representations and/or modalities. The central server can provide access by a number of patients as well as a number of health care professionals and/or insurance carriers and/or regulator agencies. Thus, the system forms a multilayered hub and spoke model with the central server and/or central database at the hub and each layer corresponding to patient's, health care providers, insurers, regulators, etc., respectively. Similarly, the implantable device and its externally related elements, may be configured or broken into elements to alternatively amplify and transmit a raw signal, raw data, processed data, data from memory, Built In Test (BIT) data, data under specific contingent situations of the body's parameters, the device's parameters, data describing specific actions of the device, or combinations thereof.

With respect to implantable devices generally, in some embodiments the devices comprise of one or more sensors generally with a corresponding transducer(s). The transducers can reduce an analog or other physical or chemical parameter signal associated with the sensor that can be subsequently converted into a digital or other electrical signal suitable for further processing if appropriate. The electrical signal can be transmitted from the body to an external receiver, for example, using wireless communication. In some representative embodiments, the signals are stored for transmission at a later time, although the signals can be transmitted intermittently without any prompting. In general, the implantable device may have a microprocessor, an appropriate power source and appropriate memory to mediate the interface between the transmitter and the sensor. In some embodiments, the implantable device can further comprise a receiver. Other embodiments have an output transducer that propagates energy in response to an electrical signal, which correspondingly may be generated in response to a biological condition, a radio transmission and electromagnetic signal or other biological or physical condition.

Drug or other chemical delivery for various implants can be facilitated through the use of micro-electromechanical systems (MEMS) or other instrumented system. In some embodiments, these drug elution devices can be programmed to deliver the therapeutic agent under prescribed conditions. For example, the drug delivery rate can be according to a programmed rate, such as a constant rate or a rate that is varied in a systematic way. Alternatively, the drug delivery parameters can be established within the device based on measurements within the device or an associated device. For example, the parameters related to drug elution rate may be physical parameter, for example, blood pressure, pulse rate or other similar parameter, or a chemical parameter, such as pH, oxygen concentration or serum glucose concentration. In some embodiments, the drug elution can be controlled through external stimulation or programming through transmitted instructions. In addition, a patient treatment protocol controlling the drug delivery rate can be occasionally evaluated, and the device's dispensing program can be reprogrammed through wireless communication with the implanted device. In some embodiments, the drug can only be dispensed upon receipt of an external signal providing an instruction to dispense the drug. In other embodiments, the action may be triggered directly in response to body chemistry, activation of a switch or through a computer algorithm.

In particular, suitable drugs can be directly applied at the site of the injury using a suitable smart dispenser. Suitable drugs can depend on the specific injury. For example, to promote bone healing, bone growth hormones can be delivered at or near the site of the injury. To promote vascularization, growth factors, such as vascular endothelial growth factors (VEGF) can be delivered locally. The total doses can be small since the drugs are applied directed to the point of need rather than systemically. Such approaches also can result in reduced or eliminated side effects. For implants designed for drug delivery to acute injuries or other conditions, the drug delivery device does not need refilling through a connection outside from the patient. Thus, the reservoir of drugs can be selected as an appropriate amount for treatment of the acute condition, such as a bone injury or an infection associated with a skeletal injury. In some embodiments, the drug delivery device can be left within the patient after it has completed dispensing of the drug if the device is sufficiently small and formed from appropriate biocompatible materials. However, in other embodiments, the drug reservoir can be refillable, such as through a tube or the like that extends out of the patient. Refillable drug systems are described further in published U.S. Patent Application US2005/0054988A to Rosenberg et al., entitled "Implantable Pump With Adjustable Flow Rate," incorporated herein by reference.

The smart medical devices can be designed to directly influence and improve the healing process. For example, the application of certain energies to a wound or injury can improve the healing event. The use of an implantable energy propagating transducer provides for the direction of the healing process directly to the location of the injury to focus the application of the therapy. Suitable energy for delivery includes, for example, heat, ultrasonic energy, RF energy and direct electrical current. Due to the direct application to the injury, the magnitude of energy can be low. Through the direct application of low levels of therapeutic energy, side effects can be reduced or eliminated. These devices can be designed for the treatment of acute conditions such that an implantable power supply provides sufficient energy through the treatment process. In alternative or additional embodiments, the device can be powered and/or recharged through application of electromagnetic radiation such that either acute or chronic conditions can be treated using energy propagating transducers.

For use with implantable devices, physical constraints on the systems provide performance guidelines for the electronics used to control the device. With respect to the power consumption if batteries are used, very thin batteries can be formed, as described further in published PCT application WO 01/35473A to Buckley et al., entitled "Electrodes Including Particles of Specific Sizes," incorporated herein by reference. These thin batteries can extend over a significant fraction of the device surface to extend the capacity of the battery. Also, if battery storage is used, the battery can be recharged using an RF signal to supply power to the device. See, for example, U.S. Pat. No. 6,166,518 to Guillermo et al., entitled "Implantable Power Management System," and Published U.S. Application 2004/0106963A to Tsukamoto et al., entitled "Implantable Medical Power Module," both of which are incorporated herein by reference.

Small radio frequency antennas can be used, or in some embodiments the antenna function can be the primary function of the device. Suitable antennas are described, for example, in U.S. Pat. No. 6,563,464 to Ballantine et al., entitled "Integrated On-chip Half-Wave Dipole Antenna Structure," and U.S. Pat. No. 6,718,163 to Tandy, entitled "Method of Operating Microelectronic Devices, and Methods of Providing Microelectronic Devices," both of which are incorporated herein by reference. Currently, the Federal Communication Commission has set aside a frequency band between 402 and 405 MHz specifically for wireless communication between implanted medical devices and external equipment. Based on the description above, the RF antenna can be incorporated on the chip with the processor, and the battery can be integrated into a device with the chip. Suitable sensors and the like are described further in published PCT application WO 00/12041 to Stark et al., entitled "Orthoses for Joint Rehabilitation," and U.S. Pat. No. 6,689,056 to Kilcoyne et al., entitled "Implantable Monitoring Probe," both of which are incorporated herein by reference.

The devices described herein can speed the healing of orthopedic injuries or diseases and/or other medical injuries or diseases through the application of therapeutic drugs or energy from an implanted device. Furthermore, the smart implantable devices can communicate measurement information about diseases or other injuries external to the patient for evaluation. The communication capabilities from and/or to the device can be interfaced with a remote communication system that can facilitate efficient application of medical care with the need for fewer office visits while providing feedback on the healing process and therapy remotely. Thus, the quality of care can be improved while increasing efficiency and lowering costs.

Patient Management Through a Central Server-Database

In general, the smart implant systems can be implemented in a basic format allowing for interfacing directly or indirectly with a health care professional in their office or other medical facility during a visit or stay. However, an implementation of the smart implant systems built upon an integrated communication system can achieve a much more effective and convenient system while possibly saving cost and achieving significantly improved patient results. In its full implementation, the system is built upon a central server or distributed servers with multiple layers of spokes extending from the server(s). The server(s) can interface with one or more databases, which can be distributed databases. Of course, in intermediate implementations, layers of spokes and/or components of the interface can be eliminated while still achieving an effective system. While the systems described herein are directed to implantable devices, the centralized management can similarly be effective with non-implantable devices as well as hand held devices that interrogate the psychological and/or pain condition of a patient through a personal computer, which may or may not be ambulatory, in conjunction with another medical device or as a stand alone treatment device. Such psychological and/or pain interrogation of the patent can have broad applicability not only in the psychological treatment of the patient but also for facilitating treatment of the patient across a range of acute and chronic medical conditions, which almost invariably have a psychological component of the recovery process. Redundant hardware, software, database and/or server components may be part of the overall system in order to ensure system reliability.

The integrated communication system organization for interfacing with smart medical devices, whether implanted or not, is summarized in FIG. 1. FIG. 1 shows both a linear communication channel involving four linked components I, II, III and IV, as well as four layers of hubs and spokes 1, 2, 3, and 4 based off of the central server(s). The hub and spoke structure is discussed after a discussion of the linked components. Communications enabled medical devices 100 can be, for example, implantable, wearable and/or otherwise ambulatory with a patient. Medical device 100 can optionally comprise a processor 102 and/or sensors 104/treatment elements 106. Medical device 100 communicates along communications channel 108. Collectively, medical device 100, processor 102 and sensors 104/treatment elements 106 can be referred to as component I, to the extent the optional elements are present.

As shown in FIG. 1, communication channel 108 communicates with a patient communications hub 120. Patient communication hub 120 can interface with a patient computer 122, which can be an ambulatory computer such as a hand held computer, which can have a patient output channel 124, such as a screen, buzzer, vibrator or speaker to communicate with the patient. Collectively, patient communication hub 120, patient computer 122 and patient output channel 124 can be referred to as component II, to the extent that optional elements are present. Patient communication hub 120 can further support entry of information through a keyboard, speaker or the like to communication information from the patient. The patient's communication hub further communicates through communications channel 126 with central server(s) 130.

Central server(s) 130 generally comprise communications elements 132, a computer system 134, a central database 136 with corresponding collected information 138, as well as algorithms and related software tools to perform a diagnosis and/or represent, evaluate, and/or modify or progress a patient's treatment protocol 138 or the like. Collectively, the central server(s) and its components can be referred to as component III, to the extent that optional components are present. Collected information within the database can comprise, for example, patient identification information, patient medical histories, medical literature, medical best practice data, institutional best practice data, patient specific data, diagnosis algorithms, treatment protocols, general treatment result summaries correlated with treatment protocols, device operating parameters, drug interaction data, and the like.

Algorithms and related software tools can comprise, for example, statistical analyses, simulation tools, workflow algorithms, and the like. Output from the central database can comprise updated patient protocol data streams that are transmitted to the smart orthopedic implant or other instrumented medical implant. Outputs can also comprise tools to help clinicians with patient treatment including progress reports for inclusion in a patient medical record, visualization tools to monitor smart implant performance and simulation tools for protocol modeling, analysis and improvement.

The Central Server can also provide maintenance and administration facilities, comprised of interactive software tools, interfaces, and/or data entry facilities to help the clinician, authorized specialists within an entity that has licensed the system such as a hospital, or the engineers of a given device's manufacturer, to set up, test, modify, or delete clinical protocols or the parameter ranges and operating characteristics associated with a particular device being managed by the system. These tools can be implemented as a simple form that lists parameters and values, visual drag-and-drop tools that enable the clinical professional to select parameters from a list of parameters and drag the selected parameters into a visual representation of the treatment protocol, or as an application program interface that allows external software tools and programs to interact with the database.

Furthermore, the central server can monitor compliance and result evaluation related to the execution of self-diagnostic algorithms within the remote instrumented medical device, whether or not an implanted device. For example, at prescribed intervals, the central server can instruct and/or interrogate the remote medical device to initiate a self-diagnostic routine or request information regarding a previously executed routine. Records on the self diagnosis can be stored for future references. If an error condition is encountered, the central server can initiate an appropriate response, such as request that the patient notify their clinician, directly notifying the clinician, reprogram the device or other appropriate response.

The Central Server can also provide tools to help with the on-going operations and administration of the system, including security administration tools to manage the access and authority permissions of system users, firewall administration facilities, network performance monitoring facilities, interfaces to other systems within a medical institution or a manufacturer, server and database performance monitoring facilities, database administration facilities, system configuration management tools, tools to manage and update the software resident on the remote managed devices, back-up and recovery tools, as well as device logging and tracking facilities, including adverse event logging capabilities for government and manufacturer monitoring, and the like.

Central server(s) 130 further communicate through communications channel 140 to a clinician station 150. Clinician's station 150 can comprise a computer with an output channel to provide notification and/or to convey received information visually, audibly, in printed output, via email, via a wireless handheld device, such as Palm Corporation's Treo or Research in Motion's Blackberry device, via interactive video conference with the patient and possibly other local or remote members of the clinician team, or otherwise to the physician, clinician or other health care professional 152. Collectively, the clinician's station and associated components can be referred to a component IV, to the extent that optional components are present.

Components (I or II) and III of the system are optional in that one or the other or both of these components can be absent. FIG. 1 easily displays the resulting simpler systems by conceptually removing the missing component and connecting the in-line communication channels to close the resulting gap. Thus, if component II is absent, component I communicates directly with component III such that communication channels 108 and 126 merge, while if component I is absent, component II servers to provide patient input directly relating to pain or psychological condition of the patient. Similarly, if component III is absent, component II communicates directly with component IV, and communication channels 108 and 140 merge. If both components II and III are absent, component I communicates directly with component IV, and communication channels 108 and 140 merge. The remote communication of pain and psychological state of a patient to health care professionals is described further in copending U.S. patent application Ser. No. 10/997,737 to Stark et al., entitled "Remote Psychological Evaluation," incorporated herein by reference.

In some embodiments, the heart of the system is the central server(s) (component III) that coordinates communication in a multiple layered spoke structure. One layer of spokes (1) extends to a plurality of patients and corresponding components I and optionally II. The patients may or may not be equipped with the equivalent medical devices as each other, and similarly the patients may or may not be evaluated for similar types of medical conditions. Thus, the treatment of a large number of patients can be monitored and coordinated through one particular central database and associated server(s). A second layer of spokes (2) indicates connections with health care professionals represented through their corresponding communication channels by component IV. A large number of health care professionals may have access to the system, and these health care professionals may or may not be located at widely dispersed geographic locations. These health care professionals may be based in professional offices, or they may be located at hospitals, clinics, home offices or the like. If a particular patient is being treated by a plurality of health care professionals or clinicians, such as physicians with different specialties, the central database can provide easy access to the data to all attending health care professionals. To maintain appropriate privacy guarantees, appropriate password or other access control can be implemented to ensure that only appropriate information is dispensed to particular persons.

To facilitate administration of the health care system at reduced costs, the system can be designed such that information on treatment and results can be forwarded to payers, including, for example, government payers, such as Medicare and Medicaid, or private insurance providers and/or other health care administrators 160 from the central database server. Generally, access would be provided to a large number of administrative entities. This communication dimension corresponds with a third layer of spokes (3). This layer of communication spokes can improve efficiency and oversight while providing expected reimbursement of the healthcare professionals with efficient processing.

Furthermore, in some embodiments, the robustness of the system warrants system review. While individual health care professionals and/or regulators 162 responsible for the overall care of a particular patient may have latitude to alter the treatment protocol for a particular patient, the range of protocols for a particular device, for example, as established by the manufacturer via engineering or clinical testing, as well as the treatment intervention function of the central database server itself, perhaps as established as clinical best practice by a health care provider that has licensed the system for internal use, generally cannot be changed in some embodiments. Food and Drug Administration regulators generally have ultimate oversight responsibilities that can be facilitated through direct access to relevant databases storing treatment outcomes and history. This practice ensures that the most accepted treatments are available to patients, such as treatment that correlate with improved treatment results. To update and continuously improve the operation of the treatment protocols and accepted automated intervention by the central server, one or more selected professionals can have the responsibility for updating and improving the protocols and automated response of the server. These professionals interact with the server to evaluate protocols, ensure quality control and review best practices. This dimension of communication channels corresponds with a fourth layer of spokes (4).

An additional role of the central system can be to provide emergency notification of a received parameter outside of an acceptable range. The particular response can be selected based on the particular condition. In some circumstances, the patient can be notified through the patient interface of the patient's computer. The patient can be told a suitable response such as go to the doctor, take a certain drug, lie down, etc. In some circumstances, an ambulance or other emergency response vehicle can be called to go to the location of the patient, and the patient can also be notified in these circumstances if appropriate. In other circumstances, a clinician can be notified, although notification of a physician, nurse, technician or other health care professional can also be ancillary to other responses above.

General Implant Structure

A general instrumented implant is shown schematically in FIG. 2A. This implant can be an orthopedic implant or other suitable medical implant, such as a drug or intervention delivery device implanted at or near an organ or other suitable location within a patient. Implant 180 can comprise, for example, one or more components, such as a frame 182, electronics 184, a sensor or sensors 186 and an output transducer 188. Electronics can comprise, for example, one or more of a power supply 192, a control circuit 194, memory 196 and a communication element 198, which can perform transmitting and/or receiving. The control circuit can comprise a microprocessor along with other analog and digital elements. In some embodiments, the controller can comprise analog and/or digital components without a microprocessor. An actual system may or may not include all of the features shown schematically in FIG. 2A. Some of the sensors can be positioned elsewhere in the body, on the surface or outside of the body of the implant to provide for appropriate measurements. Similarly, the electronic components may or may not be packaged in the same physical location with appropriate communication between separate components. Desired placement of various electronic and physical elements may be determined based on technical, medical or anatomic considerations. Similarly, the implants can be components of an implant system that have physically separate frames and other functional components. Thus, a plurality of implant components can be spaced apart within the patient while maintaining communication between the components. For example, a plurality of implants can each comprise a frame, a controller and a transducer, in which the separate implants have wired or wireless communication between the implants. Thus, one implant can comprise a measurement transducer such that the measurements are communicated to the other implant that comprises a therapeutic transducer, which may alter the therapeutic parameters based on the measurements. In other embodiments, one or more implants may comprise a plurality of transducers.

The frames can be formed from a range of materials, such as metals, ceramics, polymers and a combination thereof. Suitable metals include, for example, a range of metals that have been used for medical applications, such as stainless steel, tantalum and various alloys, for example, shape memory alloys, spring metal alloys and/or Nitinol®, a nickel titanium alloy. As used herein, metal refers to metal elements in a metallic form, generally substantially unoxidized. Metal may be selected based on mechanical and/or electromagnetic properties. Suitable polymers include, for example, elastomers and plastics, such as polyethylene, polypropylene, polyurethanes, polyesters, and the like. The frames can be formed partially or completely from a bioresorbable polymer, such as those known in the art, for example, homopolymers or copolymers of lactic acid, glycolic acid and acetic acid. More complex frames may have a substructure with elements, such as wire, laminations, voids, mechanical elements, and/or electronic or magnetic active or passive elements. The materials can be processed, for example, using conventional techniques, such as extrusion, molding, machining, calendering, and combinations thereof. The structure may be configured to effectuate particular selected functions of the devices, as described in detail herein.

In some embodiments, the frame can be configured for placement at or near an organ, such as an endocrine organ. For placement at or near an organ, the implant can be relatively thin and gently curved such that it can be place along the surface of the organ without injuring the organ. The size can be selected as appropriate for a particular organ. The device can comprise a therapeutic transducer, such as a drug delivery transducer or an energy propagating transducer, such that the therapeutic effect can be concentrated at the organ, which relates directly to the concept of being configured for placement at or near an organ.

Figure 2B:
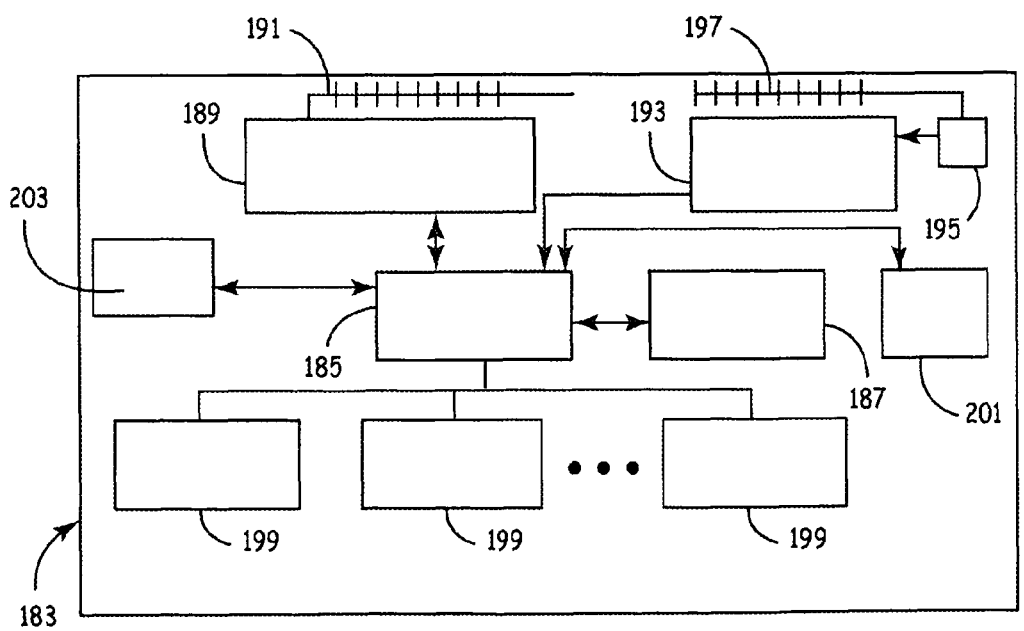
FIG. 2B is a schematic diagram of the electronics module and other electrical components suitable for use with selected embodiment of an implantable medical device.

A schematic diagram of the interconnections of electrical components within a smart orthopedic implant or other smart implantable device is shown in FIG. 2B. These devices can be placed within a single platform or housing, split between a plurality of platforms or housings, or directly mounted on a device or set of devices at suitable locations and with suitable connections. Referring to FIG. 2B, electronic architecture 183 comprises a central processor 185 operably connected to a memory device 187, which can be volatile and/or non-volatile memory, transmitter/receiver 189 with antenna 191 and power supply/battery 193, which can be connected to a charge device 195 and optional antenna 197 to received external recharging. Furthermore, processor 185 can be connected optionally to various transducers, such as one or more measurement/input transducers 199, a drug delivery device 201, which can comprise a MEMS transducer or the like, and/or other output transducers 203, such as a device that outputs therapeutic energy.

For embodiments, the implant can comprise a coil that can function as an induction coil for receiving an RF signal or a magnetic field. Polymer can be used to provide structural features and appropriate electrical insulation. Thus, the coil can function as an antenna. The coil as an antenna can be electrically connected to suitable transmitter and/or receiver. In addition, the electromagnetic interaction with a metal coil can be used to direct an electric current in association with the implant. This can be used, for example, to recharge a battery or to direct a current into tissue or to directly power a device, such as a pacing device, defibrillation device or other implantable device. The field applied to the coil can be a static field or an oscillating field, such as an RF field. A magnetic field can be applied with the magnets of an MRI instrument or other magnetic or electromagnet to induce a current. In some embodiments, an electrical current can be used to stimulate drug release either through a MEMS effect or by initiating the biodegradation of a polymer associated specifically with an appropriate portion of the drug delivery structure. Similarly, such coil structures or the like can be implanted within or on a prosthetic vessel to provide comparable functions.

As noted above, the instrumented implants can be orthopedic implants or other desired implants. Some representative orthopedic implant structures are shown in FIGS. 3-8. A wide variety of additional implant structures can be designed based on these representative examples.

Figure 3:
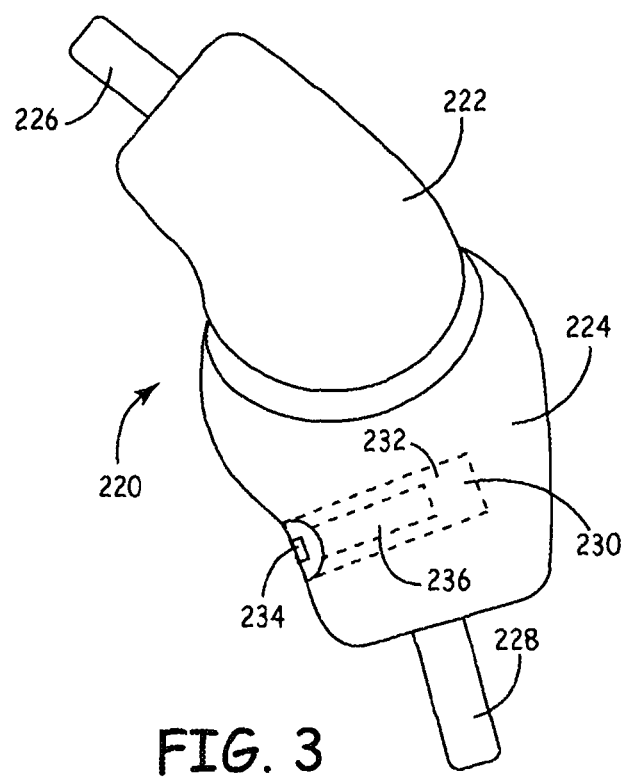
FIG. 3 is a schematic perspective view of an instrumented prosthetic replacement joint.

Referring to FIG. 3, a prosthetic replacement joint 220 comprises a first joint element 222, a second joint element 224, implant posts 226, 228 and an instrumented element 230. The designs of first joint element 222, second joint element 224 and implant posts 226, 228 can be based on any suitable design. A wide range of commercial prosthetic joints are available including, for example, ankles, shoulders, fingers, knees, and hips, which can each be instrumented based on the disclosure herein. Representative prosthetic joints are described further, for example, in U.S. Pat. No. 6,413,279 to Metzger et al., entitled "Floating Bearing Knee Joint Prosthesis With A Fixed Tibial Post," U.S. Pat. No. 6,162,253 to Conzemius et al., entitled "Total Elbow Arthroplasty System," and U.S. Pat. No. 6,676,706 to Mears et al., entitled "Method And Apparatus For Performing A Minimally Invasive Total Hip Arthroplasty," all three of which are incorporated herein by reference. Instrumented element 230 comprises a frame 232, surface transducer 234 and electronics compartment 236. Surface transducer can be a measurement sensor(s) and/or a therapy application transducer(s). Instrumented element 230 may not have a surface transducer if the functional elements are all internal to the element, and in some embodiments instrumented element 230 can comprise additional surface transducers and/or internal transducers that are not exposed to the surface. Electronics compartment 236 can have suitable electronic components, generally in electrical connection with surface transducer 234 if present, such as the electrical components in FIG. 2B, although some of the electrical components may be implanted separate from instrumented element 230 either associated with prosthesis 220 or not and with suitable wired or wireless connections.

Figure 4:
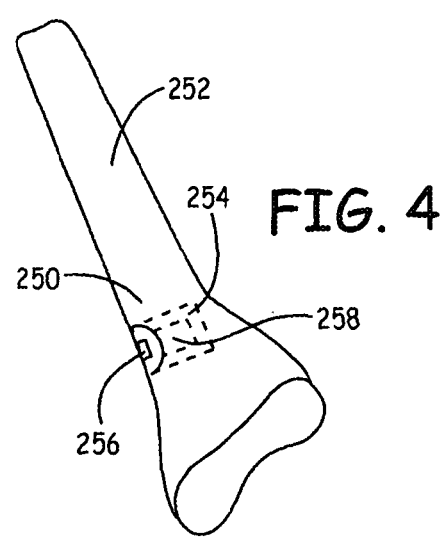
FIG. 4 is a perspective view of an instrumented orthopedic implant that is designed for insertion into a bone.

Referring to FIG. 4, orthopedic implant 250 is placed within a native bone 252. Implant 250 can be somewhat analogous to instrumented element 230 in FIG. 3, although placement within a native bone raises certain complications relative to placement within a prosthesis. Referring to FIG. 4, implant 250 comprises a frame 254, a surface transducer 256 and electronics compartment 258 with appropriate associated electronics, such as the electronics components describe with respect to FIG. 2B.

Figure 5:
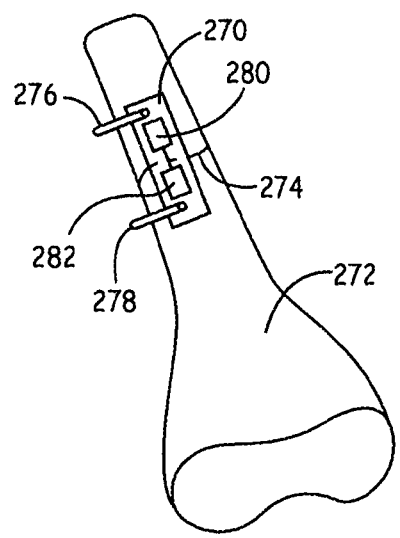
FIG. 5 is a perspective view of an orthopedic implant that is designed for attachment to the surface of a bone.

Referring to FIG. 5, in other embodiments, an implantable orthopedic device 270 is designed for association with a fractured or broken bone 272 in the vicinity of the injury 274. Device 270 can be a component in an internal fixation system, such as a plate or the like. Device 270 can be held in place with pins 276, 278, adhesives and/or the like. Implantable orthopedic device 270 can comprise selected electronics 280 and associated one or more transducers 282. Selected electronics 280 can include, for example, a microprocessor, a communication system with transmitting and/or receiving capabilities, a power supply, memory and the like. Transducers 282 can include, for example, measurement transducers, such as those described above, energy propagating transducers, drug delivery transducers or other therapeutic transducers. In some embodiments, measurement transducers can comprise strain gauges that measure strain within the device, which can be related to stress exerted on the healing bone.

Figure 6:
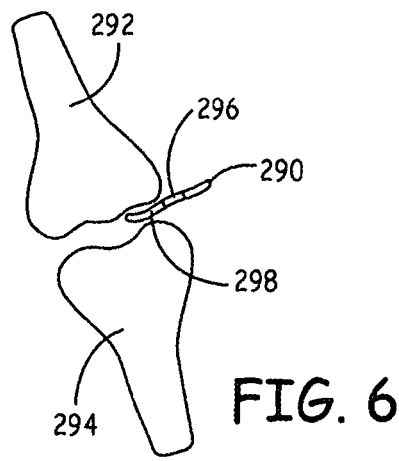
FIG. 6 is a schematic side view of an orthopedic implant designed for placement within a joint.

In additional or alternative embodiments, the orthopedic implant is designed for insertion between two bones at a joint. Referring to FIG. 6, orthopedic implant 290 is designed to fit between bones 292 and 294. Orthopedic implant 290 can comprise, for example, selected electronics 296 and associated one or more transducers 298. Selected electronics can include, for example, a communication system, a microprocessor, memory and the like. Suitable transducers 298 can be treatment delivery transducers and/or measurement transducers, such as pressure sensors, strain gauges or the like.

Figure 7:
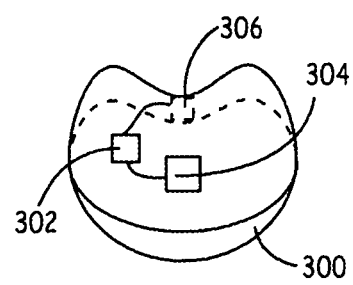
FIG. 7 is a perspective view of an instrumented prosthetic disc.

Another representative embodiment of an instrumented orthopedic implant is shown in FIG. 7. In this embodiment, prosthetic disc 300 is designed for replacement of a damaged disc of a patient. Prosthetic disc 300 can comprise, for example, electronics 302 and associated transducers 304, 306. Electronics can comprise, for example, a microprocessor, a communication system with transmitting and/or receiving capabilities, a power supply, memory and the like. Transducers 304, 306 can be, for example, pressure sensors to measure pressures within the disc at the spinal cord or between disc, for example. However, transducers 304, 306 can also be, for example, therapeutic transducers and/or other measurement transducers. Similarly, prosthetic disc 300 can comprise only one transducer or more than two transducers as desired. Disc 300 can be based, for example, on designs of existing commercial prosthetic discs, such as the Charité™ artificial disc commercially sold by DePuy Spine, Inc.

Figure 8:
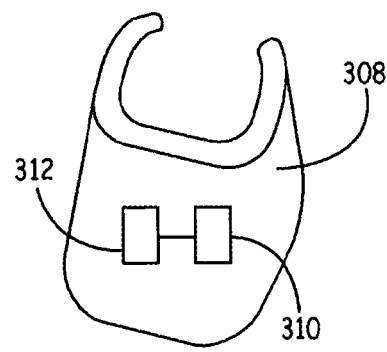
FIG. 8 is a perspective view of an instrumented spinal fusion cage.

Referring to FIG. 8, an instrumented spinal fusion cage 308 has one or more transducers 310 and associated electronics 312 operably connected to the transducers with wired or wireless connections. Suitable transducers are described above and can be measurement transducers and/or therapeutic transducers. Associated electronics can include, for example, a microprocessor, a communication system with transmitting and/or receiving capabilities, a power supply, memory and the like.

External Controller

In general, an external controller coordinates collection of data from the implant, the communication method of the implant, communication of instructions to the implant and communication between the instrument and health care professionals and may comprise an appropriate amplifier for signals received from an implantable device. A standard microcomputer or workstation with an appropriate processor/microprocessor can be adapted for use as an external communicator through the connection of an appropriate transmitter and/or receiver to the computer through a suitable port. In some embodiments, the external coordination instrument comprises an ambulatory communicating and/or computing device, such as a personal digital assistant, for example, a Treo™, Blackberry™ or other similar commercial devices, adapted for this use or a specially designed hand held device.

Figure 9:
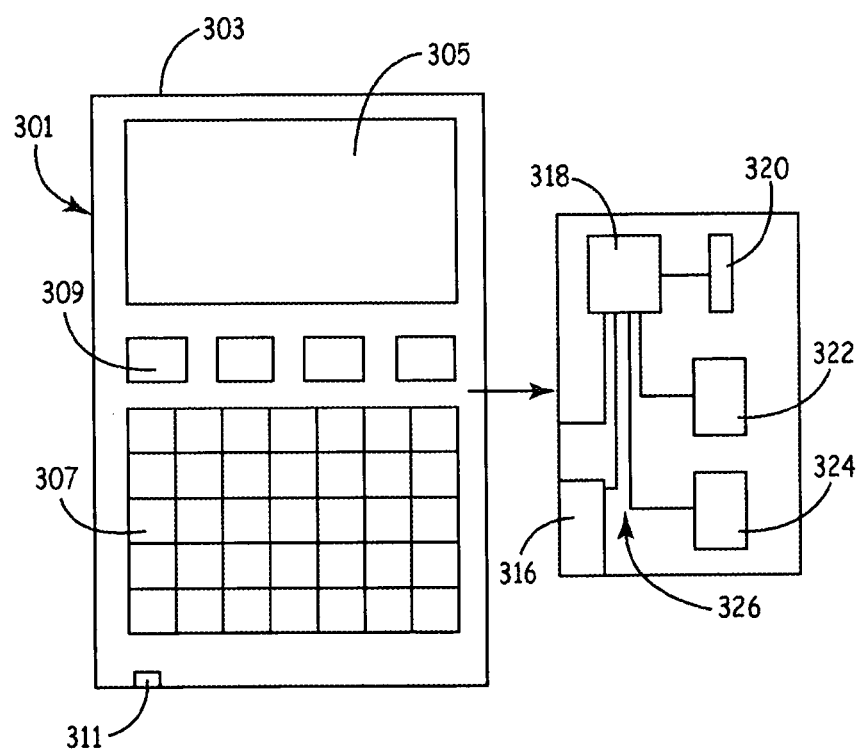
FIG. 9 is a top view of hand held computer/personal digital assistant for patient use to interface with a medical device and/or a remote central server, with an insert on the right schematically depicting one embodiment of the interconnections of electrical components.

A suitable device is shown schematically in FIG. 9. External controller 301 comprises a case 303, a display 305, a keyboard 307, additional optional switches 309 and one or more optional ports 311, such as USB, ethernet, a power supply port and other suitable ports. A schematic depiction of one embodiment the interior of the device is shown in the insert of FIG. 9. As shown in the embodiment of the insert, controller 300 comprises a power supply 316, a processor 318, additional memory 320, a receiver 322, a transmitter 324 and suitable buses 326 to interconnect the components.

A separate antenna can be attached if desired to facilitate receiving and/or transmitting a weak signal from an implanted device. Some possible additional features of the device is described further in published PCT application WO 00/12041 to Stark et al., entitled "Orthoses for Joint Rehabilitation," incorporated herein by reference. Use of sensors with external orthopedic devices is described further in published PCT application WO 00/12041 to Stark et al., entitled "Orthoses for Joint Rehabilitation," and in U.S. Pat. No. 6,540,707 to Stark et al., entitled "Orthoses," both of which are incorporated herein by reference. These sensors and associated electronics can be adapted for use within implants based on the description herein. Energy propagating transducers are described further for external orthopedic devices, which can be adapted for implantable based on the teachings herein, in published PCT application WO 96/36278 to Stark, entitled "An Orthopedic Device Supporting Two Or More Treatment Systems and Associated methods," incorporated herein by reference.

In general, controller of the implanted medical device and/or the hand held controller of FIG. 9 can be remotely monitored and or reprogrammed. In general, the hand held controller and/or a laptop and/or table top computer can be used to network the system for communication with a remote healthcare professional, such as a physician, and/or with a central monitoring station with a central database, which can be useful for remote reprogramming and/or self-adjustment via data collection and application of appropriate algorithms. The network can be a dedicated network/communication channel, the internet/world-wide-web, other existing networks or a yet to be developed network. Communication can be through satellite, microwave transmission, radio transmission, acoustic, phone lines, optical fiber, other electrical wire, a combination thereof or the like. Suitable control and communication protocols for medical devices, their networking and database manipulations are described further in the patents and applications described above and incorporated herein by reference. For both the controller for the implanted device and for the hand held controller of FIG. 3, security codes can be used to restrict instructions from unauthorized sources that can alter the performance of the devices in an inappropriate way.

Drug Delivery Systems and MEMS Applications

As described above, implantable medical devices are suitable for the delivery of drugs, other compounds and the like. Microelectromechanical (MEMS) devices are particularly suited for control of the delivery of bioactive agents, such as drugs or other pharmacological agent, within small devices. MEMS devices within small implantable medical devices can also be used for the performance of measurements and/or for the delivery of other treatments. MEMS devices can be considered transducers within the context of the general figures above relating to smart implantable medical structures. Other release systems for bioactive agents can be directly controlled through the application of an electric field, as described further below.

Figure 10:
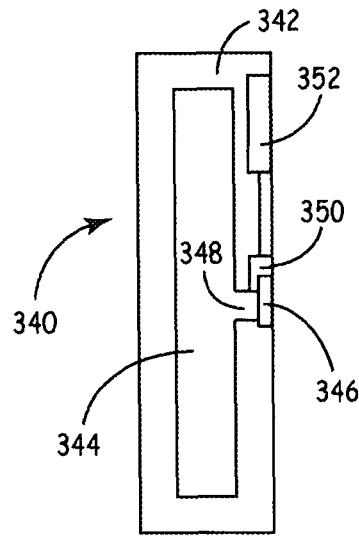
FIG. 10 is a sectional view of a MEMS based drug delivery system with the section taken through the center of the MEMS device.

An implantable medical device capable of controlled drug delivery is shown schematically in FIG. 10. Implantable device 340 comprises a frame 342, a reservoir of a bioactive agent 344, a cover 346 that blocks an opening 348 into reservoir 344 in a closed configuration, a MEMS device 350 that is operably connected to cover 346 and an electronics module 352 operably connected to MEMS device 350. Frame 342 can be a orthopedic frame or other convenient implantable frame. Reservoir 344 can hold a bioactive agent, such as a drug, in a suitable form for delivery into a patient. The bioactive agent can be in a form that slowly dissolves into the blood stream upon contact, a composition with a sufficient viscosity such that the composition diffuses slowly from the reservoir, or other suitable form for controlled delivery. Cover 346 can be made from a suitable material, such as a metal, an elastomer polymer, a ceramic or a combination thereof. The MEMS device is constructed to open and close the cover to allow for disbursal of the bioactive agent. The electronics module can be based on the electronics components described above.

Suitable drugs/bioactive agents include, for example, antimicrobial agents, hormones, cytokines, growth factors, hormone releasing factors, transcription factors, infectious agents or vectors, antithrombogenic agents, anti-restenosis agents, calcium channel blockers, antirestenosis agents, such as pacitaxel and sirolimus, blood pressure reducing agents, an acid, a base, a magnetizing agent, a polarizing agent, a targeting agent, an imaging marker, a radioactive material, an immunological agent, such as an immunoglobulin or interferon, ionic forms thereof, combinations thereof and the like. The bioactive agent can be encapsulated and/or associated with a time release composition. Many of these drugs are protein based, and other protein based drugs can be used as well as the nucleic acids coding for these drugs. Formulations for controlled delivery are well known in the art. Biological formulations generally comprise fillers, conditioners, diluents, controlled release agents, carriers and the like, which may be well known in the art. Further discussion of bioactive agent/drug formulations is found, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol. 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.), incorporated by reference for their teachings on suitable formulations of bioactive agents.

The MEMS device can be programmed, for example, using Aspect Oriented Programming, Object Oriented Programming or other industry standard techniques to open the cover to expose a drug or release the agent chemically or physically within the reservoir to the surrounding fluid for controlled delivery of the drug/therapeutic agent. An acoustically actuated MEMS device suitable for this application is described further in published U.S. patent application 2002/0017834A to MacDonald, entitled "Acoustically Actuated MEMS Devices," incorporated herein by reference. Similarly, a MEMS based pump element can be used. Suitable MEMS pumps are described in U.S. Pat. No. 6,531,417 to Choi et al., entitled "Thermally Driven Micro-Pump Buried In A silicon Substrate and method For Fabricating the Same," and published U.S. Patent Application 2004/0073175 to Jacobson et al., entitled "Infusion System," both of which are incorporated herein by reference. These systems can be used to open and close the drug reservoir, or prepare or release the bioactive agent, or provide a substrate or sink for collecting bodily chemicals, therapeutic agents or toxins.

For placement in a blood vessel or other vessel within the patient, the medical structures described above with respect to FIGS. 2-8 can be adapted to incorporate a MEMS device described herein. The MEMS devices are described above and can be adapted for other mechanical applications within the implantable devices. For example, a MEMS structure can be used to dislodge deposits built up on or in the device for removal in a suitable procedure.

Electric fields can be used directly for drug delivery release from micro-reservoirs covered with appropriate electrically responsive materials. The reservoirs can be formed using microfabrication techniques, such as photolithography and other conventional techniques. A matrix for the bioactive agent in the reservoir can comprise a polymer. Suitable biodegradable polymers include, for example, polyamides, poly (amino acids), poly(peptides), polyesters, copolymers thereof, and mixtures thereof. Suitable non-degradable polymers include, for example, polyethers, polyacrylates, polymethacrylates, polyurethanes, cellulose, derivatives thereof, copolymers thereof and mixtures thereof. Suitable cap materials can dissolve upon application of a current. Suitable materials include, for example, gold, silver, zinc and erodable polymer gels. Suitable release systems from micro-reservoirs adaptable for implantable devices are described further, for example, in U.S. Pat. No. 6,875,208B to Santini Jr., et al., entitled, "Microchip Devices With Improved Reservoir Opening," U.S. Pat. No. 6,123,861 to Santini Jr., et al., entitled Fabrication of Microchip Drug Delivery Devices," and U.S. Pat. No. 6,858,220B to Greenberg et al., entitled Implantable Microfluidic Delivery System Using Ultra-Nanocrystalline Diamond Coating," all three of which are incorporated herein by reference. A medical device structure can comprise a plurality of reservoirs, such as two, five, ten or more, with comparable caps such that the release of the individual reservoirs can be controlled individually as desired.

Implants with Energy Propagating Transducers

Figure 11:
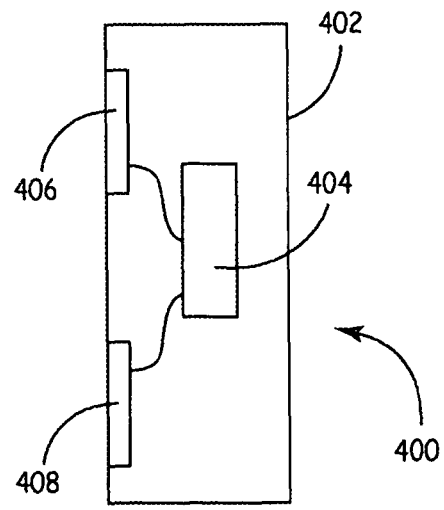
FIG. 11 is a schematic side view of a medical implant with energy propagating transducers.

An implant with energy propagating transducers is shown in FIG. 11. Implant 400 comprises a frame 402, electronics 404, a first energy propagating transducer 406 and a second energy propagating transducer 408. Frame 402 can be designed with respect to shape and size based on the selected particular location for implantation. Implant 400 may or may not be an orthopedic implant designed to interface with the patient's skeletal system. Electronics 404 generally comprises components that may or may not be packaged together within implant 400. Electronics 404 can comprise one or more electrical components described above, such as, a microprocessor, an energy source, a communication system with transmitting and/or receiving capabilities and/or memory. Suitable energy propagating transducers 406, 408 include, for example, ultrasound transducers, heaters, and electrodes. Energy propagating transducers 406, 408 can be placed along the surface of implant 400 to facilitate transmission of the propagating energy from the implant.

Ultrasound transducers can comprise, for example, a piezoelectric material, such as barium titanate or quartz. Small ultrasound transducers suitable for adaptation for the implantable devices described herein are described, for example, in U.S. Pat. No. 6,641,540 to Fleischman et al., entitled "Miniature Ultrasound Transducer," incorporated herein by reference. Suitable heater include, for example, electrical resistance heaters and/or infrared diodes. Infrared diodes are described further in U.S. Pat. No. 6,783,260 to Machi et al., entitled "IR Laser Based High Intensity Light," incorporated herein by reference. For electrodes, transducers 406, 408 can be used for opposite poles of two electrodes. These can be used for delivery of a continuous or alternating current. Implant 400 can include a single energy propagating transducer in some embodiments or three or more energy propagating transducer in further embodiments.

The embodiments described above are intended to be illustrative and not limiting. Additional embodiments are within the claims below. Although the present invention has been described with reference to specific embodiments, workers skilled in the art will recognize that changes may be made in form and detail without departing from the spirit and scope of the invention. In addition, the terms including, comprising and having as used herein are intended to have broad non-limiting scope. References cited above are incorporated to the extent that they are not inconsistent with the explicit disclosure herein.

What we claim is:

1. A biocompatible implant device comprising:
   a drug delivery device comprising:
      a drug reservoir configured to hold a drug therein; and
      a transducer configured to control delivery of the drug; and
   a microprocessor configured to:
      control transmission of implant data corresponding to a condition within a patient to a central server that comprises a database;
      receive instructions from the central server regarding a future operation of the implant device, wherein the instructions are based on an evaluation of the transmitted implant data; and
      control the transducer,
      wherein the received instructions reprogram the microprocessor relating to the control of the delivery of the drug.

2. The implant device of claim 1, wherein the transducer is a treatment transducer, and wherein the implant device further comprises:
   a communications system operably connected to the microprocessor having both transmit and receive capabilities;
   a measurement transducer operably connected to the microprocessor; and
   wherein the drug delivery device further comprises:
      a drug delivery mechanism that includes at least one of a cover and a pump, wherein the drug delivery mechanism is operably connected to the treatment transducer.

3. The implant device of claim 2, wherein the cover comprises an electrically responsive material.

4. The implant device of claim 2, further comprising a frame that mechanically supports the microprocessor, the communications system, the measurement transducer, and the treatment transducer.

5. The implant device of claim 2, wherein the measurement transducer is selected from the group consisting of a chemical sensor, a temperature sensor, a position sensor, a strain gauge, an accelerometer, or a combination thereof.

6. The implant device of claim 2, wherein the measurement transducer comprises a strain gauge, a pressure sensor, a volume sensor, a variable resistance sensor, or a combination thereof.

7. The implant device of claim 1, wherein the instructions are automatically prepared by a processor.

8. A biocompatible implant device comprising:
   a transducer configured to deliver energy to a site within a patient;
   a microprocessor configured to:
      control transmission of implant data corresponding to the condition within the patient to a central server that comprises a database;
      receive instructions from the central server regarding a future operation of the implant device, wherein the instructions are based on an evaluation of the transmitted implant data; and
      control the transducer,
      wherein the received instructions reprogram the microprocessor relating to the control of the delivery of the energy.

9. The implant device of claim 8, wherein the transducer is selected from the group consisting of an ultrasonic transmitter, a heater, an electromagnetic transmitter, an electrode, and an electroporous membrane.

10. The implant device of claim 8, wherein the transducer is selected from the group consisting of an infrared emitting diode, a radio frequency emitter, and a piezoelectric element.

11. The implant device of claim 9, wherein the transducer is a first energy propagating transducer and the device further comprises a second energy propagating transducer.

12. The implant device of claim 11, further comprising:
   a communications system operably connected to the microprocessor having both transmit and receive capabilities; and
   a measurement transducer operably connected to the microprocessor.

13. The implant device of claim 12, further comprising a frame that mechanically supports the microprocessor, the communications system, the measurement transducer, and the first and second energy propagating transducers.

14. The implant device of claim 13, wherein the measurement transducer is selected from the group consisting of a chemical sensor, a temperature sensor, a position sensor, a strain gauge, an accelerometer, or a combination thereof.

15. The implant device of claim 14, wherein the measurement transducer is selected from the group consisting of a strain gauge, a pressure sensor, a volume sensor, a variable resistance sensor, or a combination thereof.

16. The implant device of claim 15, wherein the instructions are automatically prepared by a processor.

17. A biocompatible implant device comprising:
   first and second energy propagating transducers configured to deliver energy to a site within a patient;
   a measurement transducer;
   a drug delivery device comprising:
      a drug reservoir configured to hold a drug therein; and
      a treatment transducer configured to control delivery of the drug;
   a microprocessor configured to:
      control transmission of implant data corresponding to the condition within the patient to a central server that comprises a database;

receive instructions from the central server regarding a future operation of the implant device, wherein the instructions are based on an evaluation of the transmitted implant data; and control the treatment transducer, the measurement transducer, and the first and second energy propagating transducers;

wherein the received instructions reprogram the microprocessor relating to the control of the delivery of the drug and delivery of the energy; and a frame configured to mechanically support the first and second energy propagating transducers, the measurement transducer, the drug delivery device, and the microprocessor.

18. The implant device of claim 17, wherein the measurement transducer is selected from the group consisting of a chemical sensor, a temperature sensor, a position sensor, a strain gauge, an accelerometer, or a combination thereof.

19. The implant device of claim 18, wherein the first and second energy propagating transducers are selected from the group consisting of an ultrasonic transmitter, a heater, an electromagnetic transmitter, an electrode, and an electroporous membrane.

20. The implant device of claim 19, wherein the instructions are automatically prepared by a processor.

* * * * *